(12) United States Patent
Takasugi et al.

(10) Patent No.: US 9,424,643 B2
(45) Date of Patent: Aug. 23, 2016

(54) IMAGE DISPLAY DEVICE, IMAGE DISPLAY METHOD, AND COMPUTER-READABLE RECORDING MEDIUM

(71) Applicant: OLYMPUS CORPORATION, Tokyo (JP)

(72) Inventors: Kei Takasugi, Hino (JP); Hidekazu Iwaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/801,060

(22) Filed: Jul. 16, 2015

(65) Prior Publication Data

US 2015/0324983 A1 Nov. 12, 2015

Related U.S. Application Data

(63) Continuation of application No. PCT/JP2014/064967, filed on Jun. 5, 2014.

(30) Foreign Application Priority Data

Sep. 9, 2013 (JP) .................................. 2013-186585

(51) Int. Cl.
*G06K 9/00* (2006.01)
*G06T 7/00* (2006.01)
(Continued)

(52) U.S. Cl.
CPC ........... *G06T 7/0012* (2013.01); *A61B 1/0002* (2013.01); *A61B 1/00009* (2013.01); *A61B 1/00045* (2013.01); *A61B 1/041* (2013.01); *G06F 11/321* (2013.01); *G06T 7/00* (2013.01);
(Continued)

(58) Field of Classification Search
None
See application file for complete search history.

(56) References Cited

U.S. PATENT DOCUMENTS

2008/0086028 A1 4/2008 Matsui
2009/0077128 A1* 3/2009 Kimoto .............. A61B 1/00045
(Continued)

FOREIGN PATENT DOCUMENTS

JP 2006-061626 A 3/2006
JP 2006-288612 A 10/2006
(Continued)

OTHER PUBLICATIONS

International Search Report dated Sep. 9, 2014 issued in PCT/JP2014/064967.
(Continued)

*Primary Examiner* — Shervin Nakhjavan
(74) *Attorney, Agent, or Firm* — Scully, Scott, Murphy & Presser, P.C.

(57) ABSTRACT

An image display device includes: a display unit; an image extraction unit that extracts a main image group from an image group; an image association unit that associates sub images included in a sub image group not extracted from the image group with main images included in the main image group; and a display control unit that generates a display screen in which the main image group is arranged in a first area along a first direction and the sub images are aligned with each of the main images in a second area along a second direction, and causes the display unit to display the display screen. The display control unit changes the display screen in a mode in which the main image group is moved along the first direction and in a mode in which the main image group and the sub image group are moved along the second direction.

14 Claims, 16 Drawing Sheets

(51) Int. Cl.
*A61B 1/04* (2006.01)
*A61B 1/00* (2006.01)
*G06F 11/32* (2006.01)

(52) U.S. Cl.
CPC ... *G06T 7/0016* (2013.01); *G06T 2207/10016* (2013.01); *G06T 2207/10068* (2013.01); *G06T 2207/30004* (2013.01); *G06T 2207/30092* (2013.01)

(56) References Cited

U.S. PATENT DOCUMENTS

| | | |
|---|---|---|
| 2010/0097392 A1 | 4/2010 | Nishiyama et al. |
| 2010/0165088 A1 | 7/2010 | Seo |
| 2010/0182412 A1* | 7/2010 | Taniguchi ............ A61B 1/041 348/65 |
| 2010/0310239 A1* | 12/2010 | Kono ................. A61B 1/00009 386/343 |
| 2012/0113239 A1* | 5/2012 | Krupnik ............ A61B 1/00009 348/65 |

FOREIGN PATENT DOCUMENTS

| | | |
|---|---|---|
| JP | 2010-094185 A | 4/2010 |
| JP | 2012-185583 A | 9/2012 |
| JP | 2013-075244 A | 4/2013 |
| JP | 5385138 B2 | 1/2014 |
| WO | WO 2009/008125 A1 | 1/2009 |

OTHER PUBLICATIONS

Decision of a Patent Grant issued in JP 2015-502427 dated Mar. 24, 2015.

* cited by examiner

IMAGE DISPLAY DEVICE, IMAGE DISPLAY METHOD, AND COMPUTER-READABLE RECORDING MEDIUM

CROSS-REFERENCE TO RELATED APPLICATIONS

This application is a continuation of PCT international application Ser. No. PCT/JP2014/064967 filed on Jun. 5, 2014 which designates the United States, incorporated herein by reference, and which claims the benefit of priority from Japanese Patent Application No. 2013-186585, filed on Sep. 9, 2013, incorporated herein by reference.

BACKGROUND

1. Technical Field

The present invention relates to an image display device including a display unit which displays a display screen, an image display method, and a computer-readable recording medium.

2. Related Art

There have been conventionally proposed capsule endoscope systems configured to use a capsule endoscope for taking images of the inside of a subject to acquire in-vivo images of the inside of the subject and allow a doctor or the like to observe the in-vivo images (for example, see Japanese Patent Application Laid-open No. 2006-288612 and Japanese Patent No. 5385138).

A capsule endoscope, when being swallowed by a mouse of a subject for observation (examination), moves through the body cavity, for example, in the organs such as the stomach and the small intestine according to their peristalses, and take images of the inside of the subject at predetermined time intervals in the course of the movement before its natural expulsion. During the movement through the body cavity, the capsule endoscope also transmits data of the images taken in the body of the subject in sequence to the outside via wireless communication.

A capsule endoscope system includes a reception device and an image display device as well as the capsule endoscope described above.

The reception device receives the image data in sequence transmitted from the capsule endoscope and records the received image data in sequence in a portable recording medium inserted into the reception device.

When the portable recording medium is inserted into the image display device, the image display device imports the image data from the recording medium. Then, the image display device displays in-vivo images corresponding to the imported image data frame by frame in succession (frame-by-frame playback).

The doctor or the like reviews the in-vivo images displayed as described above to make a diagnosis on the subject.

SUMMARY

In some embodiments, an image display device includes: a display unit that displays a display screen; an image extraction unit that extracts a main image group from an image group, the image group including a plurality of images acquired in a time-series manner, and the main image including main images satisfying a specified condition; an image association unit that associates each of sub images included in a sub image group not extracted by the image extraction unit from the image group with each of the main images included in the main image group; and a display control unit that generates a display screen in which the main image group is arranged in a first area in a time-series manner along a first direction and each of the sub images associated with each of the main images by the image association unit is aligned with each of the main images in a second area different from the first area in a time-series manner along a second direction orthogonal to the first direction, and causes the display unit to display the display screen. The display control unit changes the display screen in a mode in which the main image group is moved along the first direction and in a mode in which at least part of the main image group and at least part of the sub image group are moved along the second direction.

In some embodiments, an image display method executed by an image display device is presented. The image display method includes: extracting a main image group from an image group, the image group including a plurality of images acquired in a time-series manner, and the main image including main images satisfying a specified condition; associating each of sub images included in a sub image group not extracted from the image group with each of the main images included in the main image group; generating a display screen in which the main image group is arranged in a first area in a time-series manner along a first direction and each of the sub images associated with each of the main images is aligned with each of the main images in a second area different from the first area in a time-series manner along a second direction orthogonal to the first direction; displaying the display screen; and changing the display screen. In the changing the display screen, the display screen is changed in a mode in which the main image group is moved along the first direction and in a mode in which at least part of the main image group and at least part of the sub image group are moved along the second direction.

In some embodiments, a non-transitory computer-readable recording medium is a recording medium with an executable program recorded therein. The program instructs a processor, which an image display device has, to execute: extracting a main image group from an image group, the image group including a plurality of images acquired in a time-series manner, and the main image including main images satisfying a specified condition; associating each of sub images included in a sub image group not extracted from the image group with each of the main images included in the main image group; generating a display screen in which the main image group is arranged in a first area in a time-series manner along a first direction and each of the sub images associated with each of the main images is aligned with each of the main images in a second area different from the first area in a time-series manner along a second direction orthogonal to the first direction; displaying the display screen; and changing the display screen. In the changing the display screen, the display screen is changed in a mode in which the main image group is moved along the first direction and in a mode in which at least part of the main image group and at least part of the sub image group are moved along the second direction.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, an image display device, an image display method, an image display program according to the present invention will be described in detail with reference to the accompanying drawings. However, the present invention is not limited to the embodiments.

First Embodiment

Schematic Configuration of an Image Display System

Figure 1:
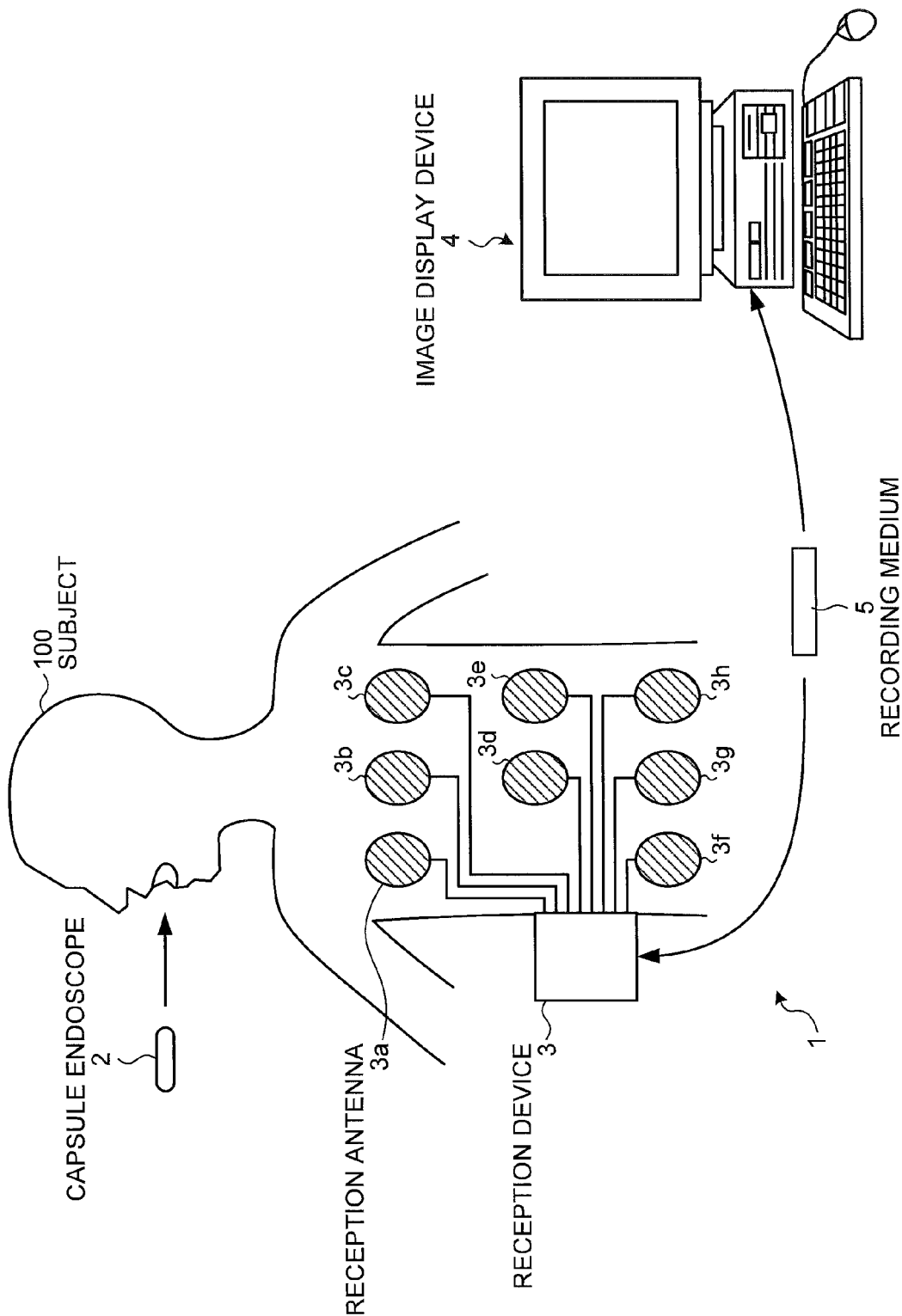
FIG. 1 is a schematic view of an image display system according to a first embodiment of the present invention.

FIG. 1 is a schematic view of an image display system 1 according to a first embodiment of the present invention.

The image display system 1 is a system that uses a swallow-type capsule endoscope 2 to acquire in-vivo images of inside of a subject 100 and allows a doctor or the like to observe the in-vivo images.

The image display system 1 includes a reception device 3, an image display device 4, a portable recording medium 5, and the like, as well as the capsule endoscope 2, as illustrated in FIG. 1.

The recording medium 5 is a portable recording medium for exchange of data between the reception device 3 and the image display device 4, which is detachably attached to the reception device 3 and the image display device 4.

The capsule endoscope 2 is a capsule endoscope device formed in a size introducible into the organs in the subject 100. The capsule endoscope 2 is introduced into the organs of the subject 100 by oral ingestion, and is moved through the organs by their peristalses or the like to take in-vivo images in sequence. Then, the capsule endoscope 2 transmits image data produced by the image taking in sequence.

The reception device 3 includes a plurality of reception antennas 3a to 3h to receive the image data from the capsule endoscope 2 in the subject 100 via at least one of the reception antennas 3a to 3h. Then, the reception device 3 accumulates the received image data in the recording medium 5 inserted into the reception device 3.

The reception antennas 3a to 3h may be disposed on the surface of the subject 100 as illustrated in FIG. 1, or may be disposed on a jacket worn by the subject 100. The number of reception antennas included in the reception device 3 may not be limited to eight as far as it is one or more.

Configuration of the Image Display Device

Figure 2:
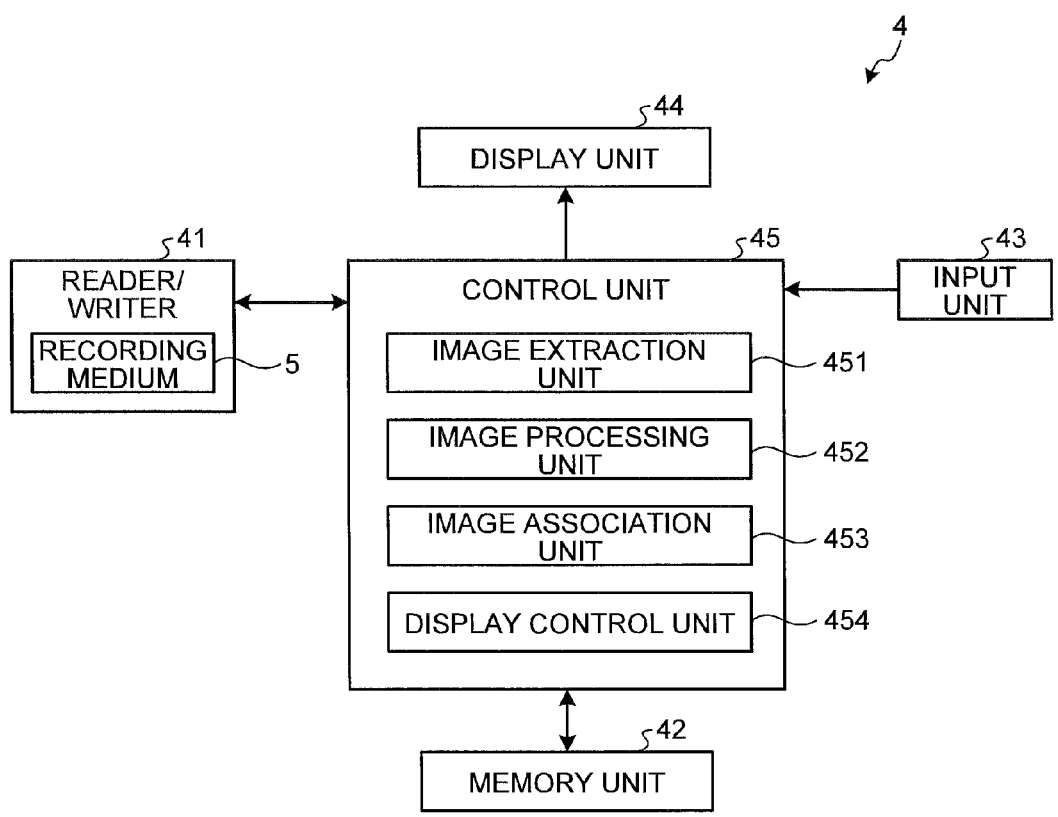
FIG. 2 is a block diagram of the image display device illustrated in FIG. 1.

FIG. 2 is a block diagram of the image display device 4.

The image display device 4 is configured as a workstation that acquires image data of the subject 100 and displays images corresponding to the acquired image data.

The image display device 4 includes, as illustrated in FIG. 2, a reader/writer 41, a memory unit 42, an input unit 43, a display unit 44, a control unit 45, and the like.

When the recording medium 5 is inserted into the reader/writer 41, the reader/writer 41 imports image data (an in-vivo image group including a plurality of in-vivo images taken (acquired) by the capsule endoscope 2 in a time-series manner) from the recording medium 5 under control by the control unit 45. The reader/writer 41 also transfers the imported in-vivo image group to the control unit 45. The in-vivo image group transferred to the control unit 45 is stored in the memory unit 42.

That is, the reader/writer 41 functions as an image acquisition unit in the present invention.

The memory unit 42 stores the in-vivo image group transferred from the reader/writer 41. The memory unit 42 also stores various programs (including an image display program) executed by the control unit 45, information necessary for processing by the control unit 45, and the like.

The input unit 43 includes a keyboard, a mouse, and the like, and accepts user operations.

The input unit 43 functions as an instruction acceptance unit in the present invention.

The display unit 44 includes a liquid display and the like, and displays a display screen including in-vivo images, under control by the control unit 45.

The control unit 45 includes a CPU (central processing unit) and the like, and reads programs (including the image display program) stored in the memory unit 42, and controls entire operations of the image display device 4 according to the programs.

The control unit 45 includes an image extraction unit 451, an image processing unit 452, an image association unit 453, a display control unit 454, and the like, as illustrated in FIG. 2.

The image extraction unit 451 extracts a main image group including main images (in-vivo images for display) satisfying a specified image extraction condition, from an in-vivo image group for display subjected to image processing by the image processing unit 452 and stored in the memory unit 42. Then, the image extraction unit 451 stores the extracted main image group in the memory unit 42.

The image extraction condition may be a threshold for degree of similarity between temporally successive in-vivo images, or the like, for example.

The image processing unit 452 performs image processing on the in-vivo images stored in the memory unit 42 to produce in-vivo images for display. Then, the image processing unit 452 stores an in-vivo image group for display including the generated in-vivo images for display in the memory unit 42.

The image processing unit 452 also calculates information necessary for the image extraction by the image extraction unit 451.

Specifically, the image processing unit 452 reads the in-vivo image group for display from the memory unit 42, and extracts color information on the in-vivo images for display. Then, the image processing unit 452 calculates the degrees of similarity between temporally successive in-vivo images for display in the in-vivo image group for display, for each of the in-vivo images for display, based on the color information on the in-vivo images for display.

The image processing unit 452 may calculate motion vectors between adjacent images in the in-vivo image group for display, and calculate the degrees of similarity between the in-vivo images for display, for each of the in-vivo images for display, based on the calculated motion vectors of the in-vivo images for display.

Then, the image processing unit 452 stores in the memory unit 42 the information on the degrees of similarity calculated as described above, in association with the corresponding in-vivo images for display.

The image association unit 453 associates each of main images included in the main image group extracted by the image extraction unit 451 with sub images (in-vivo images for display) included in the sub image group not extracted by the image extraction unit 451 from the in-vivo image group for display. Then, the image association unit 453 stores in the memory unit 42 association information indicative of association of the main images in association with the sub images.

The display control unit 454 reads the information stored in the memory unit 42 according to user operations on the input unit 43, generates a display screen on which the main images or the sub images are arranged, and displays the display screen on the display unit 44.

Operations of the Image Display Device

Next, operations of the image display device 4 (image display method) will be described.

Figure 3:
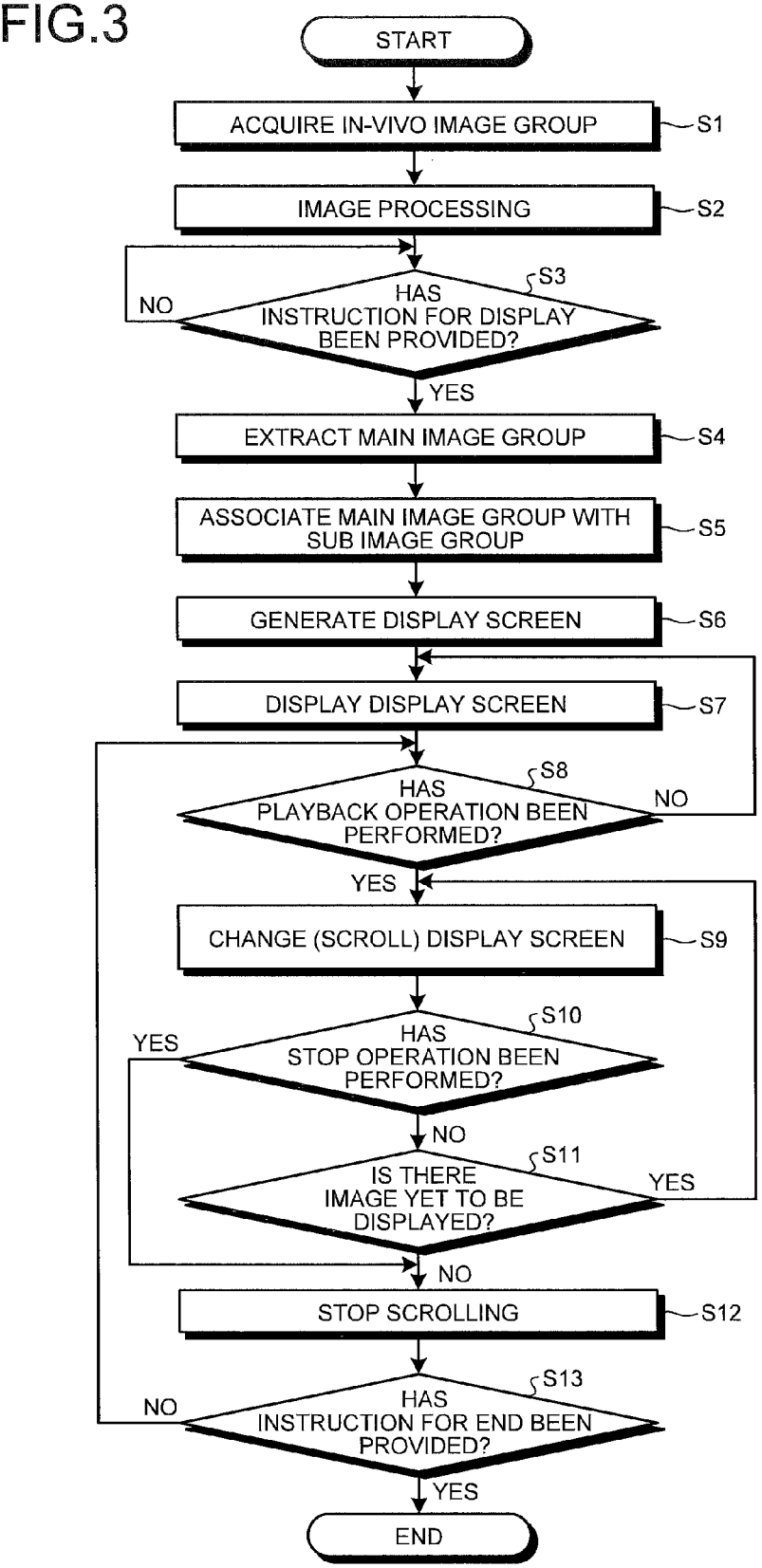
FIG. 3 is a flowchart of an image display method according to the first embodiment of the present invention.

FIG. 3 is a flowchart of an image display method according to the first embodiment of the present invention.

First, when the recording medium 5 is inserted into the reader/writer 41, the reader/writer 41 imports the in-vivo image group from the recording medium 5 under control by the control unit 45 (step S1: image acquisition step). Then, the in-vivo image group imported by the reader/writer 41 is stored in the memory unit 42.

Subsequently, the image processing unit 452 reads the in-vivo image group from the memory unit 42, and generates an in-vivo image group for display by image processing. The image processing unit 452 also extracts color information on the in-vivo images for display, and calculates the degrees of similarity between temporally successive in-vivo images for display in the in-vivo image group for display, for each of the in-vivo images for display, based on the color information (step S2). Then, the image processing unit 452 stores in the memory unit 42 information on the calculated degrees of similarity in association with the corresponding in-vivo images for display.

Subsequently, the control unit 45 constantly monitors whether the user has performed an operation on the input unit 43 to provide an instruction for display of the in-vivo images (step S3).

When it is determined that the user has provided an instruction for display of the in-vivo images (step S3: Yes), the image extraction unit 451 reads from the memory unit 42 the information on the degrees of similarity between the in-vivo images for display. The image extraction unit 451 also extracts in-vivo images for display with the degrees of similarity equal to or lower than a specified threshold (in-vivo images for display with the lower degrees of similarity between the temporally successive in-vivo images for display) from the in-vivo image group for display stored in the memory unit 42 (step S4: image extraction step). Then, the image extraction unit 451 stores in the memory unit 42 a main image group including the extracted main images.

Subsequently, the image association unit 453 associates each of the main images extracted at step S4 with sub images not extracted at step S4 (step S5: image association step). Then, the image association unit 453 stores in the memory unit 42 association information indicative of association with the main images, in association with the sub images.

Specifically, the image association unit 453 grasps the number of frames of the sub images between the temporally successive main images. When the number of frames is an even number, the image association unit 453 associates the temporal front half of the sub images with the immediately preceding main images, and associates the temporal second half of the sub images with the immediately following main images.

For example, when the in-vivo images for display of first and fourth frames in the in-vivo image group for display are main images, the number of frames of sub images between the main images is the even number "2." Therefore, the image association unit 453 associates the sub image of the second frame with the main image of the first frame, and associates the sub image of the third frame with the main image of the fourth frame.

Meanwhile, when the number of frames of sub images between temporally successive main images is an odd number, the image association unit 453 sorts the sub images into temporally former sub images and temporally latter sub images, such that the number of frames of the temporally latter sub images is larger by one. Then, the image association unit 453 associates the temporally former sub images with the immediately preceding main images, and associates the temporally latter sub images with the immediately following main images.

For example, when the in-vivo images for display of fourth and eighth frames in the in-vivo image group for display are main images, the number of frames of sub images between the main images is the odd number "3." Therefore, the image association unit 453 associates the sub image of the fifth frame with the main image of the fourth frame, and associates the sub images of the sixth and seventh frames with the main image of the eighth frame.

When the number of frame of sub image between temporally successive main images is "1," the sub image is associated with the immediately following main image.

Subsequently, the display control unit 454 generates a display screen as described below, based on the information stored in the memory unit 42 (the main image group, the sub image group, and the association information) (step S6).

Figure 4:
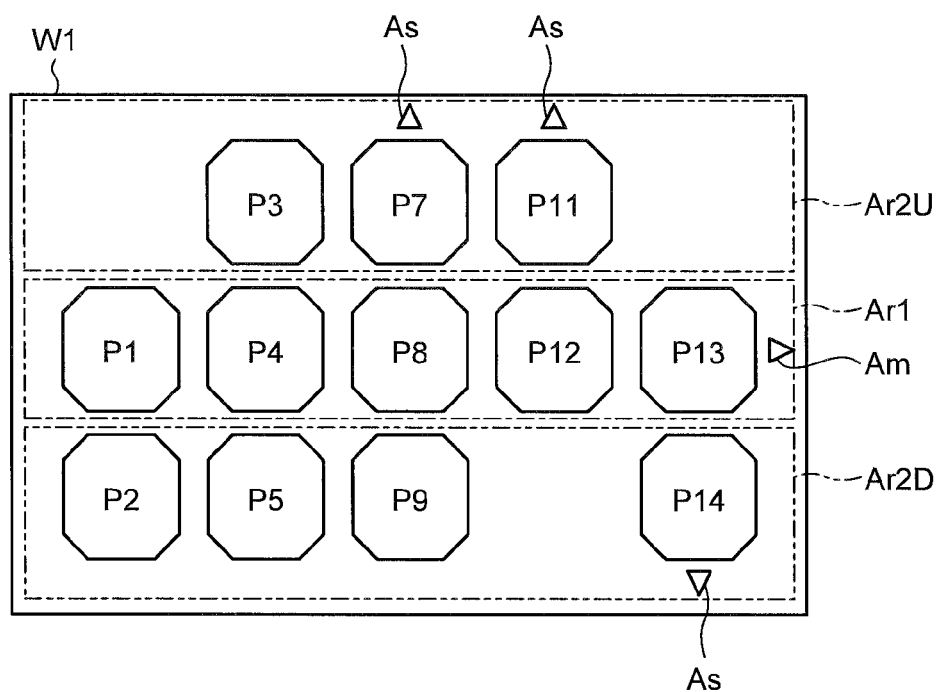
FIG. 4 is a diagram illustrating one example of a display screen generated at step S6 described in FIG. 3.

FIG. 4 is a diagram illustrating one example of a display screen W1 generated at step S6 described in FIG. 3.

Referring to FIG. 4, octagonal shapes constitute in-vivo images for display, "PX" in the in-vivo images for display indicates the in-vivo image for display of Xth frame (for example, "P8" refers to the in-vivo image for display of the eighth frame).

Specifically, the display control unit 454 reads sequentially from the memory unit 42 the main images of five frames in increasing order of frame number. Then, the display control unit 454 arranges the main images of five frames at predetermined spacings in a time-series manner in a first area passing through the center position of the display screen and extended in a horizontal direction (along a first direction).

For example, when main images of five frames P1, P4, P8, P12, and P13 are arranged in increasing order of frame number, the display control unit 454 reads the main images P1, P4, P8, P12, and P13 from the memory unit 42. The display control unit 454 arranges the main images P1, P4, P8, P12, and P13 in a time-series manner from the left in a first area Ar1 of the display screen W1 as illustrated in FIG. 4.

The display control unit 454 also reads sub images associated with the read main images of five frames, based on the association information stored in the memory unit 42. Then, the display control unit 454 arranges the sub images associated with the main images at predetermined spacings in a time-series manner, so as to be aligned with the main images, in a second area different from the first area of the display screen, in a second direction orthogonal to the first direction.

The display control unit 454 arranges the sub images associated with the main images and temporally anterior to the main images, in a second area above the main images (hereinafter, referred to as second upper area) in the display screen. The display control unit 454 also arranges the sub images associated with the main images and temporally posterior to the main images, in a second area below the main images (hereinafter, referred to as second lower area) in the display screen. Further, when there are two or more frames of sub images associated with the main images and temporally anterior or posterior to the main images, the display control unit 454 arranges only the sub images temporally nearest the main images in the second upper area or the second lower area.

As described above, when arranging a sub image group, the display control unit 454 arranges each of the sub images associated with the main images by the image association unit 453, in the second area.

For example, a sub image P2 is associated with the main image P1 and is temporally posterior to the main image P1. Accordingly, as illustrated in FIG. 4, the display control unit 454 arranges the sub image P2 below the main image P1 in a second lower area Ar2D below the first area Ar1 of the display screen W1.

In addition, for example, sub images P6 and P7 are associated with the main image P8 and are temporally anterior to the main image P8. That is, there are the two images of sub images associated with the main image P8 and temporally anterior to the main image P8. Accordingly, as illustrated in FIG. 4, the display control unit 454 arranges the sub image P7 temporally nearest the main image P8, above the main image P8, in a second upper area Ar2U above the first area Ar1 of the display screen W1, and does not arrange the sub image P6 in the display screen W1.

As described above, when the main images P1, P4, P8, P12, and P13 of five frames are arranged in increasing order of frame number, the display control unit 454 arranges sub images P3, P7, and P11 above the main images P4, P8, and P12 (in the second upper area Ar2U) of the display screen W1, respectively, and arranges sub images P2, P5, P9, and P14 below the main images P1, P4, P8, and P13 (in the second lower area Ar2D) of the display screen W1, respectively, as illustrated in FIG. 4.

Further, when any of the in-vivo image group for display stored in the memory unit 42 is not arranged in the display screen, the display control unit 454 arranges in the display screen a playback icon for prompting display of the in-vivo image for display.

In the example of FIG. 4, for instance, the sub image P6 associated with the main image P8, a sub image P10 associated with the main image P12, and a sub image P15 associated with the main image P13 are not arranged in the display screen W1. Accordingly, the display control unit 454 arranges playback icons As for prompting display of the sub images P6, P10, and P15 at positions where the sub images P6, P10, and P15 are to be arranged (above the sub images P7 and P11 and below the sub image P14) in the display screen W1.

In addition, main images of sixth and subsequent frames in the main image group are not arranged in the display screen W1. Accordingly, the display control unit 454 arranges a playback icon Am for prompting display of the main images of sixth and subsequent frames at positions where the main images of sixth and subsequent frames are to be arranged (right of the main image P13) in the display screen W1.

The foregoing playback icons Am and As are equivalent to existence information according to the present invention.

Subsequently, the display control unit 454 displays the generated display screen W1 on the display unit 44 (step S7).

The steps S6 and S7 described above are equivalent to a display step according to the present invention.

Subsequently, the display control unit 454 determines whether the user has performed a playback operation on the input unit 43 (step S8).

The playback operation here refers to an operation of positioning the mouse cursor on one of the playback icons As and Am and pressing the mouse button.

When it is not determined that playback operation has been performed (step S8: No), the display control unit 454 continues to display the display screen W1 at step S7.

Meanwhile, it is determined that a playback operation has been performed (step S8: Yes), the display control unit 454 changes (scrolls) the display screen W1 as described below (step S9: display change step).

Figure 5:
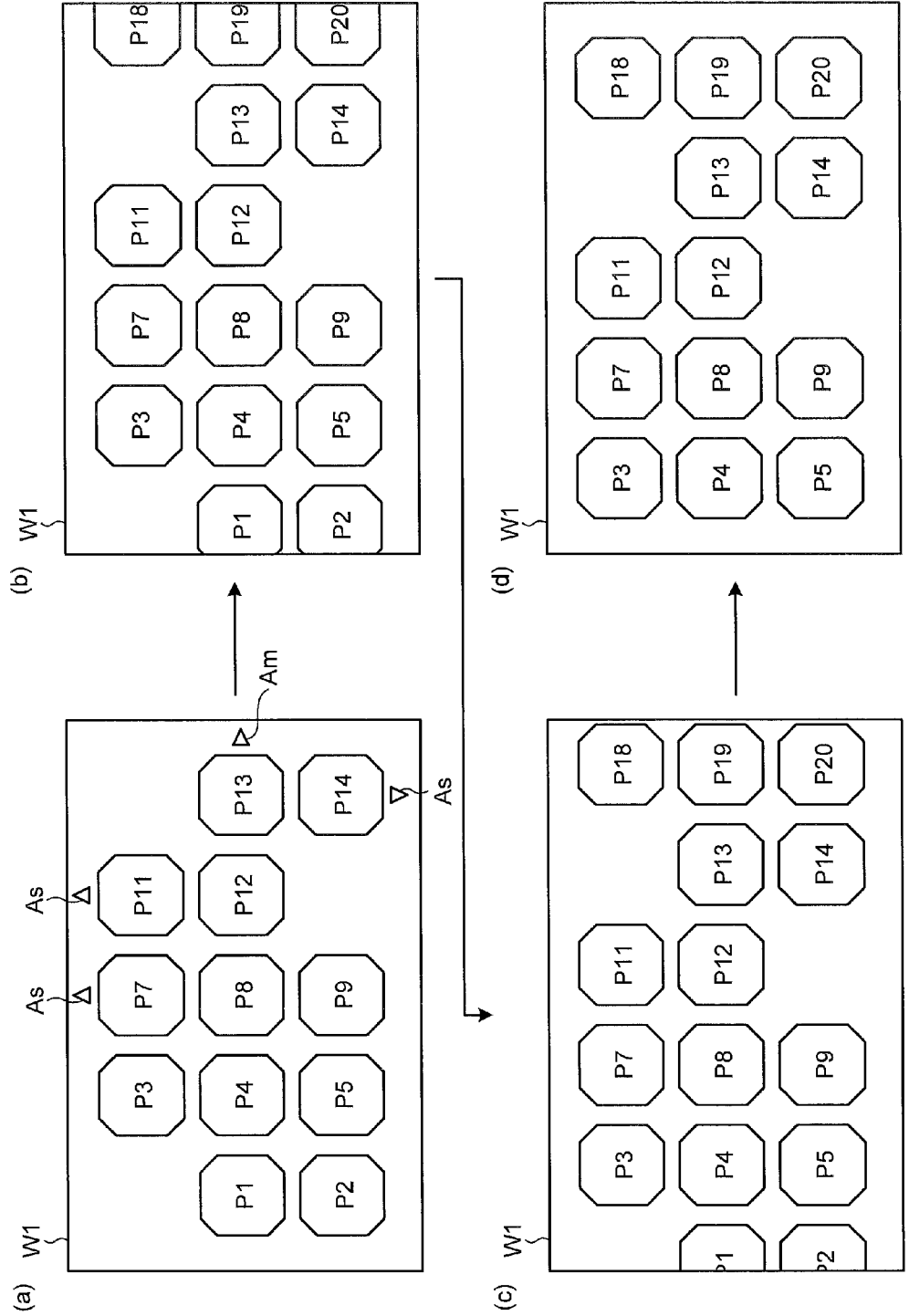
FIG. 5 is a diagram illustrating one example of screen transitions in the display screen at step S9 described in FIG. 3.
Figure 6:
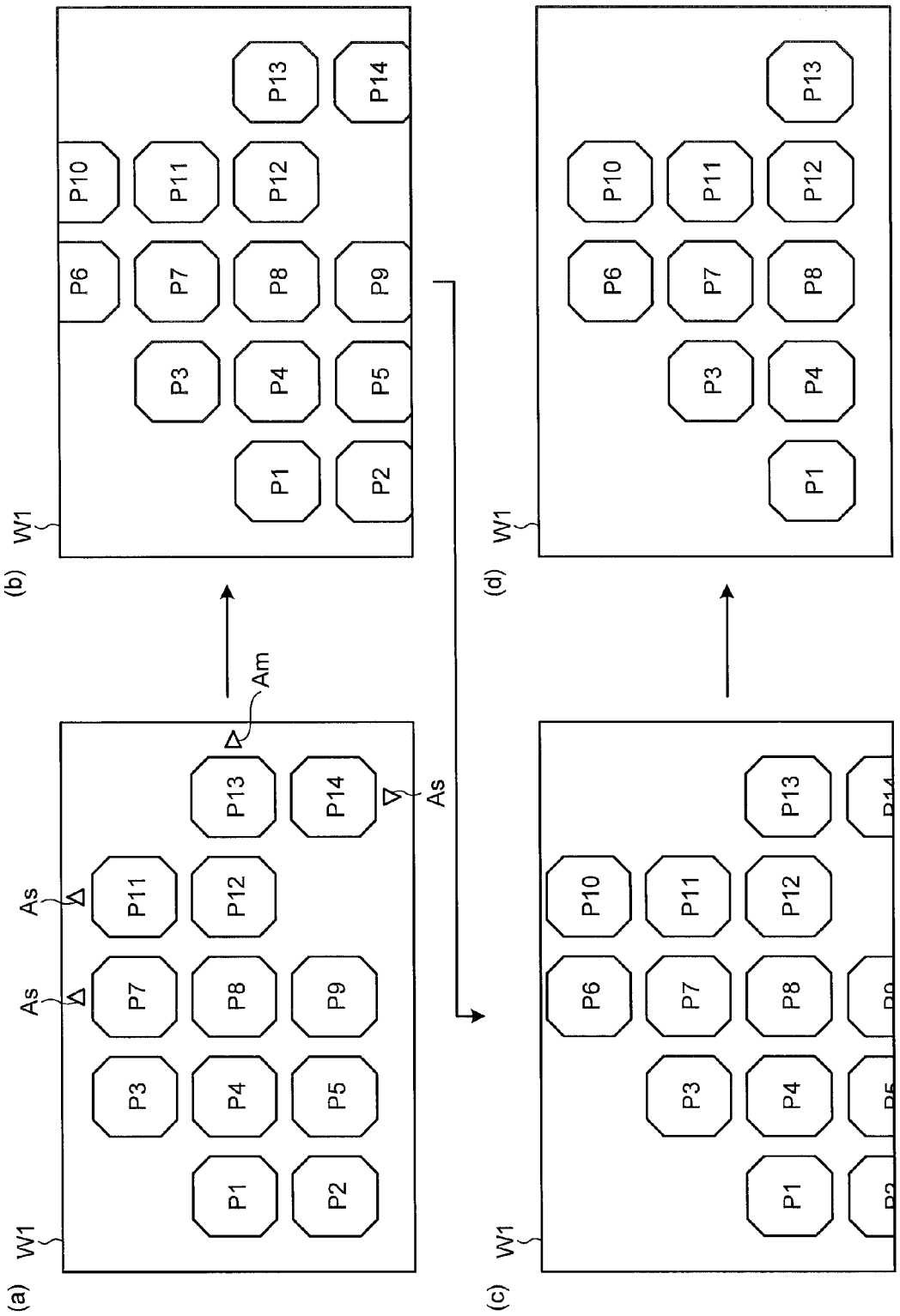
FIG. 6 is a diagram illustrating one example of screen transitions in the display screen at step S9 described in FIG. 3.

FIGS. 5 and 6 are diagrams each illustrating one example of screen transitions in the display screen W1 at step S9.

FIGS. 5 and 6 illustrate screen transitions in the display screen W1 illustrated in FIG. 4 ((a) of FIG. 5 and (a) of FIG. 6 are identical to FIG. 4). FIG. 5 represents the case where the playback icon Am has been operated, and FIG. 6 represents the case where the playback icon As has been operated.

Specifically, when the playback icon Am at the left or right end of the display screen W1 has been operated, the display control unit 454 scrolls the display screen W1 in a mode in which the main images and the sub images are integrally moved in the rightward or leftward direction.

For example, when the playback icon Am at the right end of the display screen W1 displayed at step S7 as illustrated in FIG. 4 has been operated, the display control unit 454 sequentially generates display screens W1 in a mode in which the main images P1, P4, P8, P12, and P13 and the sub images P2, P3, P5, P7, P9, P11, and P14 are integrally moved to the left.

At that time, the display control unit 454 generates the display screens W1 in which the main image P1 and the sub image P2 associated with the main image P1 are gradually displaced from the left side of the display screen W1, and the main image P19 temporally posterior to the main image P13 and the sub images P18 and P20 associated with the main image P19 gradually appear from the right side of the display screen W1.

Then, the display control unit 454 displays in the display unit 44 the generated display screens W1 illustrated in (b), (c), and (d) of FIG. 5 in sequence according to the display frame rate of the display unit 44. As described above, by sequentially displaying the display screens W1 in the display unit 44, the display screen W1 is scrolled in a mode in which the main images and the sub images are moved smoothly to the left.

Meanwhile, when the playback icon As arranged in the upper or lower side of the display screen W1, the display control unit 454 scrolls the display screen W1 in a mode in which the main images and the sub images are integrally moved in the upward direction or the downward direction (along the second direction orthogonal to the first direction).

For example, when the playback icon As above the sub image P7 in the display screen W1 displayed at step S7 as illustrated in FIG. 4 has been operated, the display control unit 454 sequentially generates display screens W1 in a mode in which the main images P1, P4, P8, P12, and P13 and the sub images P2, P3, P5, P7, P9, P11, and P14 are integrally moved downward as illustrated in FIG. 6.

At that time, the display control unit 454 generates the display screens W1 in which the sub images P2, P5, P9, and P14 in the lower side of the display screen W1 are gradually displaced from the lower side of the display screen W1, and the sub images P6 and P10 associated with the main images P8 and P12 in the display screen W1 but not arranged in the display screen W1 gradually appear from the upper side of the display screen W1.

Then, the display control unit 454 sequentially displays in the display unit 44 the generated display screens W1 illustrated in (b), (c), and (d) of FIG. 6 according to the display frame rate of the display unit 44. By sequentially displaying the display screens W1 in the display unit 44, the display screen W1 is scrolled in a mode in which the main images and the sub images are moved smoothly downward.

At that time, the display control unit 454 does not arrange the playback icons Am and As in the display screen W1 while the display screen W1 is scrolled as illustrated in (b) to (d) of FIG. 5 or (b) to (d) of FIG. 6.

Figure 7:
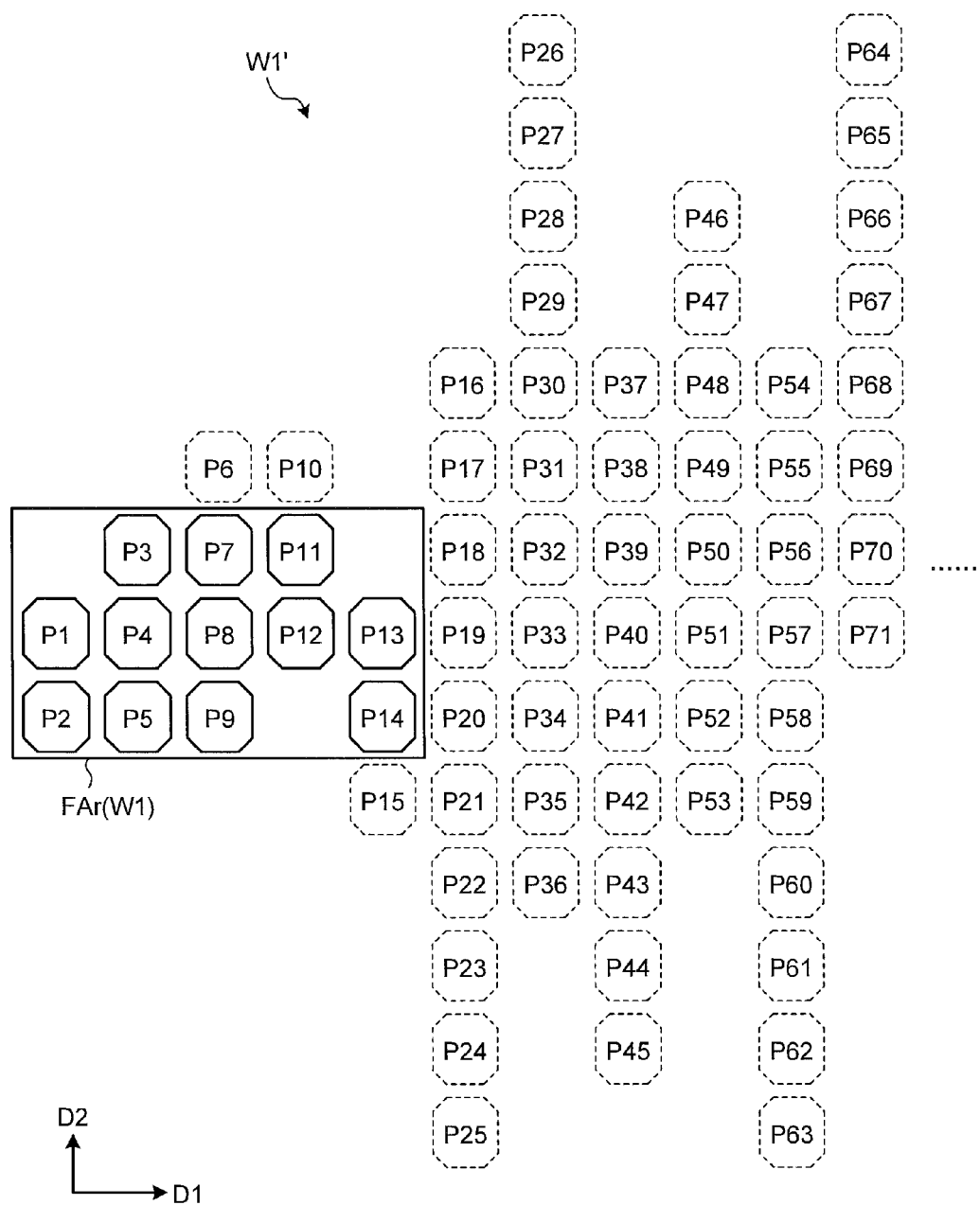
FIG. 7 is a virtual representation of step S9 described in FIG. 3.

FIG. 7 is a virtual representation of step S9.

FIG. 7 illustrates in-vivo images P1 to P71 of first to 71th frames.

The step S9 described above can be virtually represented as illustrated in FIG. 7.

As illustrated in FIG. 7, for example, a virtual screen W1' is configured such that main images P1, P4, P8, P12, P13, P19, P33, P40, P51, P57, and P71 are arranged at predetermined spacings in a time-series manner along the first direction D1, and sub images associated with these main images are arranged at predetermined spacings in a time-series manner along the second direction D2 so as to be aligned with the main images.

Then, at step S9 described above, according to operation on the playback icon Am or As, while an image area FAr is moved along the first direction D1 or the second direction D2 on the virtual screen W1', a portion of the virtual screen W1' (including main images and sub images) positioned in the image area FAr is displayed as a display screen W1 in the display unit 44.

In the first embodiment, as illustrated in FIG. 7, all of the images including the main images and the sub images arranged in the display screen W1 are of the same size.

Returning to FIG. 3, after step S9, the display control unit 454 determines whether the user has performed a stop operation on the input unit 43 (step S10).

The stop operation here refers to clicking on the mouse button while the display screen W1 is scrolled at step S9.

When it is not determined that the stop operation has been performed (step S10: No), the display control unit 454 determines whether there is any main image or sub image to be displayed by scrolling the display screen W1 (step S11).

Then, it is determined that there is any main image or sub image to be displayed (step S11: Yes), the display control unit 454 moves to step S9 to continue scrolling of the display screen W1.

Meanwhile, it is determined that the stop operation has been performed (step S10: Yes) or there is no more main image or sub image to be displayed (step S11: No), the display control unit 454 stops the scrolling of the display screen W1 (step S12).

Figure 8:
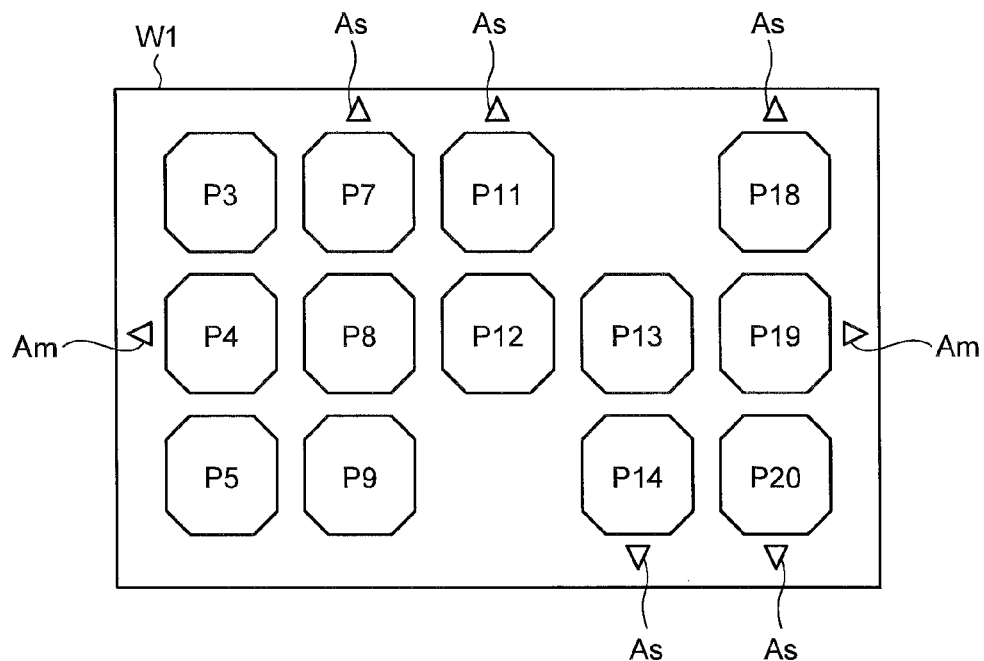
FIG. 8 is a diagram illustrating one example of a display screen displayed in a display unit at step S12 described in FIG. 3.
Figure 9:
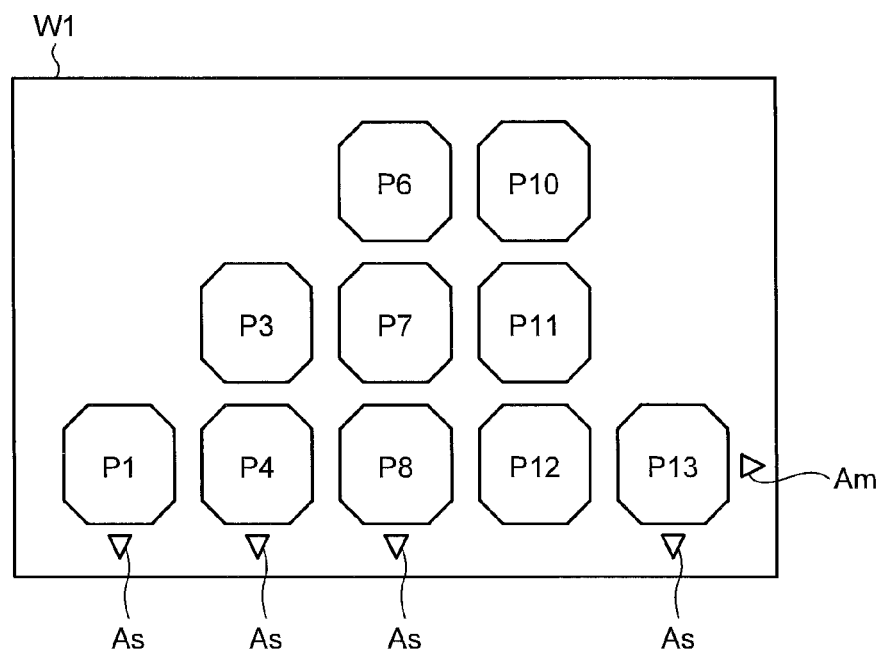
FIG. 9 is a diagram illustrating one example of a display screen displayed in the display unit at step S12 described in FIG. 3.

FIGS. 8 and 9 are diagrams each illustrating one example of a display screen W1 displayed in the display unit 44 at step S12.

FIG. 8 illustrates the display screen W1 displayed in the display unit 44 when the mouse button is clicked in the state illustrated in (d) of FIG. 5 while the display screen W1 is scrolled along the first direction D1. FIG. 9 illustrates the display screen W1 displayed in the display unit 44 when, as a result of the scrolling of the display screen W1 along the second direction D2, there is no more sub image to be displayed (the state illustrated in (d) of FIG. 6).

For example, when the mouse button is clicked while the display screen W1 is scrolled along the first direction D1, the display control unit 454 generates the display screen W1 in which the playback icons Am and As are arranged in the display screen W1 displayed in the display unit 44 by the click operation, and displays the display screen W1 in the display unit 44 as illustrated in FIG. 8.

In the example of FIG. 8, the sub image P6 associated with the main image P8, the sub image P10 associated with the main image P12, the sub image P15 associated with the main image P13, and the sub images P16, P17, and P21 to P25 associated with the main image P19 (refer to FIG. 7) are not arranged in the display screen W1. Accordingly, the display control unit 454 arranges playback icons As for prompting display of the sub images P6, P10, P15 to P17, and P21 to P25 at positions where the sub images P6, P10, P15 to P17, and P21 to P25 are to be arranged (above the sub images P7, P11, and P18 and under the sub images P14 and P20) in the display screen W1 as illustrated in FIG. 8.

In addition, the main images of first, seventh, and subsequent frames in the main image group are not arranged in the display screen W1. Accordingly, the display control unit 454 arranges playback icons Am for prompting display of the main images of first, seventh, and subsequent frames at positions where the main images of first, seventh, and subsequent frames are to be arranged (at the left side of the main image P4 and the right side of the main image P19) in the display screen W1 as illustrated in FIG. 8.

In addition, when, as a result of scrolling of the display screen W1 along the second direction D2, there is no more sub image to be displayed, for example, the display control unit 454 generates the display screen W1 in which the playback icons Am and As are arranged in the display screen W1 displayed in the display unit 44 until there is no more sub image to be displayed, and displays the display screen W1 in the display unit 44 as illustrated in FIG. 9.

In the example of FIG. 9, the sub image P2 associated with the main image P1, the sub image P5 associated with the main image P4, the sub image P9 associated with the main image P8, and the sub images P14 and P15 associated with the main image P13 are not arranged in the display screen W1. Accordingly, the display control unit 454 arranges the playback icons As for prompting display of the sub images P2, P5, P9, P14, and P15 at positions where the sub images P2, P5, P9, P14, and P15 are to be arranged (below the main images P1, P4, P8, and P13) in the display screen W1 as illustrated in FIG. 9.

In addition, the main images of sixth and subsequent frames in the main image group are not arranged in the display screen W1. Accordingly, the display control unit 454 arranges the playback icon Am for prompting display of the main images of sixth and subsequent frames at positions where the main images of sixth and subsequent frames are to be arranged (at the right side of the main image P13) in the display screen W1 as illustrated in FIG. 9.

Returning to FIG. 3, after step S12, the control unit 45 determines whether the user has performed an operation on the input unit 43 to provide an instruction for ending display of the in-vivo images (step S13).

When it is not determined that the instruction for ending display of the in-vivo images has been provided (step S13: No), the control unit 45 moves to step S8.

Meanwhile, when it is determined that the instruction for ending display of the in-vivo images has been provided (step S13: Yes), the control unit 45 terminates this process (process for displaying the in-vivo images).

According to the first embodiment described above, the image display device 4 includes the image extraction unit 451. This allows the image display device 4 to extract unusual images of a bleeding site, a lesion, or the like in the subject 100, as main images, from the in-vivo image group taken in a time-series manner by the capsule endoscope 2 (the in-vivo image group for display processed by the image processing unit 452).

According to the first embodiment, the image display device 4 also includes the display control unit 454. This allows the doctor or the like to observe the display screen W1 in which a main image group including unusual images is arranged in a time-series manner along the first direction D1. In addition, the display screen W1 is scrolled in a mode in which the main image group is moved along the first direction D1, and even when the unusual images are limited in number (for example, only one frame), the display time of the unusual images (the time at which the unusual images are moved in the display screen during scrolling) is relatively long, which makes it easier for the doctor or the like to find the unusual images. Further, even though the unusual images are not extracted as main images, the unusual images are arranged as sub images in the second upper and lower areas Ar2U and Ar2D of the display screen W1, which allows the doctor or the like to find the unusual images.

From the foregoing matter, according to the first embodiment, the image display device 4 provides the advantage that, even when unusual images included in an in-vivo image group taken by the capsule endoscope 2 in a time-series manner are limited in number, the display screen W1 can be displayed such that the unusual images are easy to find.

According to the first embodiment, the image display device 4 also includes the image association unit 453 that associates sub images not extracted by the image extraction unit 451 with main images with the frame numbers nearest those of the sub images. Then, when arranging a sub image group in the second upper and lower areas Ar2U and Ar2D, the display control unit 454 arranges each of the sub images associated with the main images by the image association unit 453 in the second upper and lower areas Ar2U and Ar2D. That is, the sub images associated with the main images are collectively arranged in the second upper and lower areas Ar2U and Ar2D.

Accordingly, when the doctor or the like finds a main image with a site of concern (an in-vivo image for display possibly representing a bleeding site, a lesion or the like, for example), he/she can review the sub images collectively arranged in the second upper and lower areas Ar2U and Ar2D and taken at the times near the time of taking the main image, compare the main image to the sub images, and check the site of concern intensively.

Further, in the first embodiment, the display control unit 454 arranges sub images associated with main images by the image association unit 453, so as to be aligned with the main images, in the second upper and lower areas Ar2U and Ar2D in a time-series manner along the second direction D2 orthogonal to the first direction D1.

Specifically, the main image group is arranged in the longitudinal center position of the display screen W1. In addition, the sub images associated with the main images are arranged such that sub images taken at the times nearer the taking times of the main images (the sub images with the frame numbers nearer the frame numbers of the main images) are positioned nearest the main images, and the sub images taken at the times more distant from the taking times of the main images (the sub images with the frame numbers more distant from the frame numbers of the main images) are positioned more distant from the main images.

Therefore, it is possible to arrange the in-vivo images for display (main images) likely to be unusual images in the display screen W1 at positions where the doctor or the like can observe most easily (the longitudinal center position). In addition, it is possible to arrange the in-vivo images for display (sub images) unlikely to be unusual images in the display screen W1 at positions distant from the longitudinal center position of the display screen W1. This allows the doctor or the like to find the unusual images more quickly.

In the first embodiment, the display control unit 454 scrolls the display screen W1 along the first direction D1, and also scrolls the display screen W1 along the second direction D2 in which the sub images are arranged.

Accordingly, when the doctor or the like finds a main image with a site of concern but some of the sub images associated with the main image are not arranged in the display screen W1, the doctor or the like can operate the input unit 43 to scroll the display screen W1 along the second direction D2 and review all of the sub images associated with the main image.

Modification Example of the First Embodiment

Figure 10:
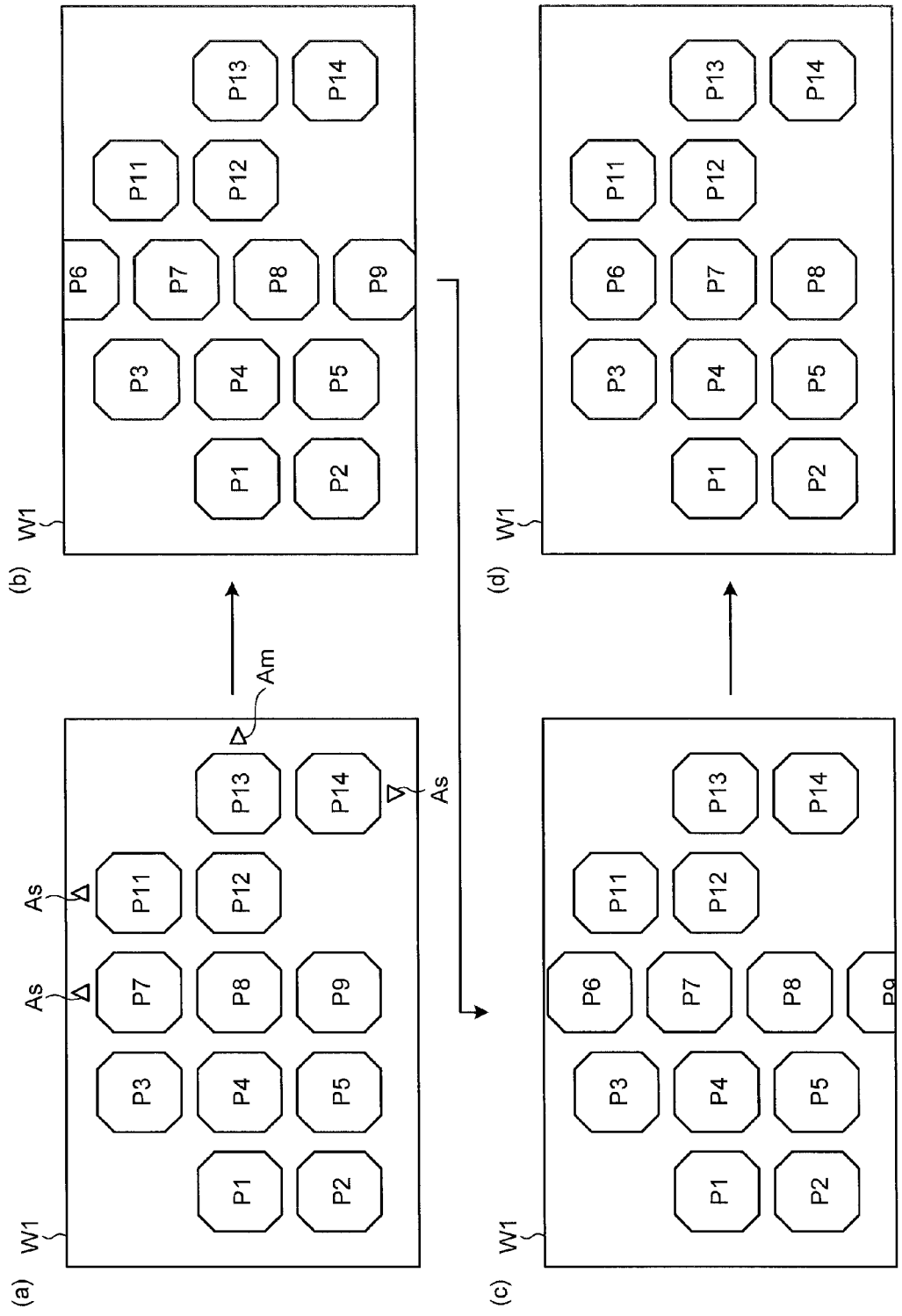
FIG. 10 is a diagram illustrating a modification example of the first embodiment in the present invention.

FIG. 10 is a diagram illustrating a modification example of the first embodiment in the present invention.

FIG. 10 illustrates screen transitions of the display screen W1 illustrated in FIG. 4 when the playback icon As is operated (the display screen W1 displayed at step S7 described in FIG. 3) ((a) of FIG. 10 is identical to FIG. 4).

In the first embodiment described above, when the playback icon As has been operated, the display control unit 454 scrolls the display screen W1 in a mode in which all of the main images and the sub images arranged in the display screen W1 are integrally moved along the second direction D2. However, the present invention is not limited to this.

The display control unit 454 may scroll the display screen W1 in a mode in which only the main images and the sub images arranged in the same column as the operated playback icon As are integrally moved in the upward direction or the downward direction (along the second direction).

For example, when the playback icon As arranged above the sub image P7 has been operated in the display screen W1 illustrated in FIG. 4 displayed at step S7, the display control unit 454 sequentially generates display screens W1 in a mode in which images P1 to P5 and P11 to P14 in columns different from that of the playback icon As are not moved, and only the main image P8 and the sub images P7 and P9 in the same column as that of the playback icon As are integrally moved downward as illustrated in (b) to (d) of FIG. 10.

At that time, the display control unit 454 generates the display screens W1 in which the sub image P9 in the lower side of the display screen W1 is gradually displaced from the lower side of the display screen W1, and the sub image P6 associated with the main image P8 in the display screen W1 but not arranged in the display screen W1 appears gradually from the upper side of the display screen W1.

Then, the display control unit 454 sequentially displays in the display unit 44 the generated display screens W1 illustrated in (b) to (d) of FIG. 10 according to the display frame rate of the display unit 44. By sequentially displaying the display screens W1 in the display unit 44 as described above, the display screen W1 is scrolled in a mode in which the main image P8 and the sub images P6, P7, and P9 in one column are moved smoothly downward.

The display control unit 454 does not arrange the playback icons Am and As in the display screen W1 during scrolling of the display screen W1 as illustrated in (b) to (d) of FIG. 10.

As described above, by scrolling the display screen W1 in a mode in which only the main image and the sub images in one column are integrally moved, it is possible to recognize more easily at one view the arrangement positions of the in-vivo images for display to be checked, as compared to scrolling the display screen W1 in a mode in which the main images and the sub images in all the columns are integrally moved as described in relation to the first embodiment.

The main images in columns different from that of the operated playback icon As (the in-vivo images for display likely to be unusual images) may be arranged in the display screen W1 even during scrolling of the display screen W1.

Second Embodiment

Next, a second embodiment of the present invention will be described.

In the following description, the same components and steps as those of the first embodiment are given the same reference signs as those of the first embodiment, and detailed descriptions thereof are omitted or simplified.

In the first embodiment, the display control unit 454 sets all images including main images and sub images in the same size in the display screen W1.

Meanwhile, in the second embodiment, main images and sub images are arranged in different sizes in the display screen W1.

The configuration of an image display system in the second embodiment is the same as that in the first embodiment.

Hereinafter, descriptions will be given as to only the sizes of main images and sub images in the display screen W1 according to the second embodiment.

Figure 11:
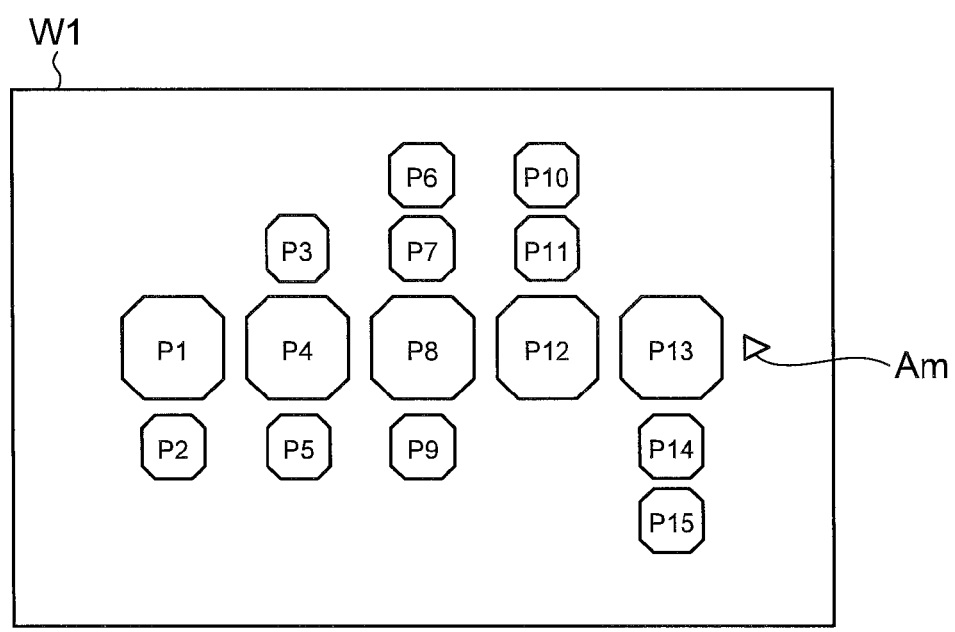
FIG. 11 is a diagram illustrating one example of a display screen generated by a display control unit according to a second embodiment of the present invention.

FIG. 11 is a diagram illustrating one example of the display screen W1 generated by the display control unit 454 according to the second embodiment of the present invention.

FIG. 11 illustrates the display screen W1 generated at step S6 described in FIG. 3.

According to the second embodiment, the display control unit 454 generates the display screen W1 in which sub images are smaller in size than main images.

The display control unit 454 sets all of the main images in the same size and all of the sub images in the same size.

For example, at step S6, the display control unit 454 generates the display screen W1 in which the sub images P2, P3, P5 to P7, P9 to P11, P14, and P15 are smaller in size than the main images P1, P4, P8, P12, and P13 as illustrated in FIG. 11.

The second embodiment is different from the first embodiment only in the sizes of the main images and the sub images, and the two embodiments are the same in how to arrange the main images and the sub images in the display screen W1 and how to scroll the display screen W1.

The second embodiment described above provides an advantage described below, as well as the same advantage as that of the first embodiment.

In the second embodiment, the display control unit 454 generates the display screen W1 in which the sub images are smaller in size than the main images.

Accordingly, by displaying the main images likely to be unusual images in a larger size than the sub images unlikely to be unusual images, the doctor or the like can take notice of the main images and find unusual images in an easier manner.

Third Embodiment

Next, a third embodiment of the present invention will be described.

In the following description, the same components and steps as those of the second embodiment are given the same reference signs as those of the second embodiment, and detailed descriptions thereof are omitted or simplified.

The third embodiment is different from the second embodiment only in that information indicative of the number of main images and sub images not arranged in the display screen W1 is arranged in the display screen W1.

The configuration of an image display device in the third embodiment is the same as that in the second embodiment.

Hereinafter, descriptions will be given as to only the information provided in the display screen W1 in the third embodiment.

Figure 12:
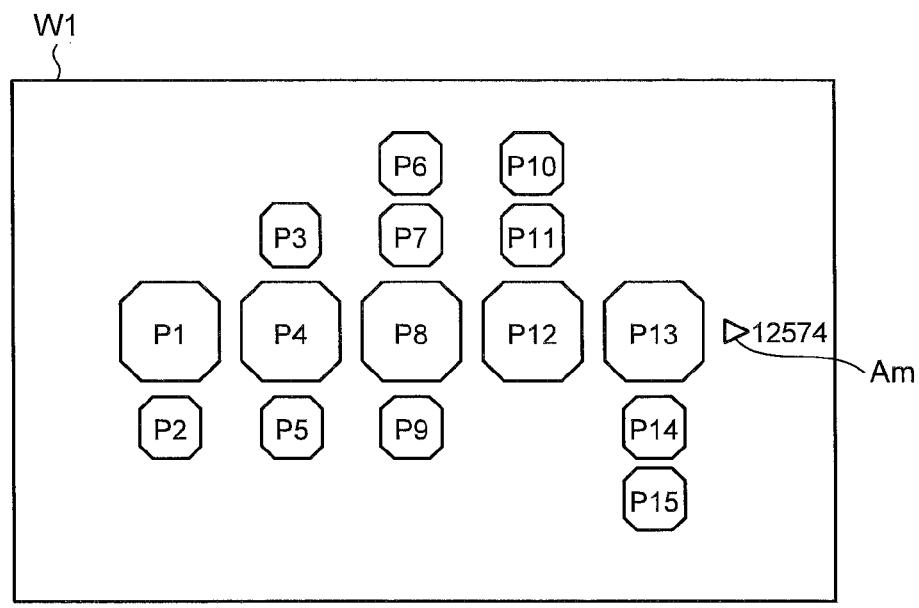
FIG. 12 is a diagram illustrating one example of a display screen generated by a display control unit according to a third embodiment of the present invention.

FIG. 12 is a diagram illustrating one example of the display screen W1 generated by the display control unit 454 according to the third embodiment of the present invention.

FIG. 12 illustrates the display screen W1 generated at step S6 described in FIG. 3.

According to the third embodiment, the display control unit 454 reads information from the memory unit 42 (a main image group, a sub image group, and association information) while the display screen W1 is not scrolled (steps S6 and S12 described in FIG. 3). Based on the information, the display control unit 454 also recognizes the number of main images not arranged in the display screen W1 and sub images associated with main images arranged in the display screen W1 but not arranged in the display screen W1, from the main image group and the sub image group stored in the memory unit 42. Then, the display control unit 454 arranges information indicative of the number at a position adjacent to the playback icon Am or As in the display screen W1.

In the example of FIG. 12, the display control unit 454 recognizes that the number of frames of main images other than the main images P1, P4, P8, P12, and P13 arranged in the display screen W1 and temporally posterior to the main images P1, P4, P8, P12, and P13 is "12574." Then, the display control unit 454 arranges the number "12574" at a position adjacent to the playback icon Am at the right end of the display screen W1.

In the example of FIG. 12, there is no sub image associated with the main images P1, P4, P8, P12, and P13 arranged in the display screen W1 but not arranged in the display screen W1. Accordingly, the display control unit 454 does not arrange the information indicative of the number of sub images or the playback icon As in the display screen W1.

The information indicative of the number is equivalent to existence information according to the present invention.

The third embodiment is different from the second embodiment only in that the information indicative of the number is arranged in the display screen W1, and the two embodiments are the same in how to arrange the main images and the sub images in the display screen W1 and how to scroll the display screen W1.

The third embodiment described above provides an advantage described below, as well as the same advantages as those of the second embodiment.

In the third embodiment, when all of main images (sub images) included in a main image group (sub image groups) are not arranged in the display screen W1, the display control unit 454 includes the information indicative of the number of the not arranged main images (sub images) in the display screen W1.

Accordingly, based on the information indicative of the number displayed in the display screen W1, the doctor or the like can scroll the display screen W1 and estimate how long it will take for reviewing all of the main images (sub images).

Fourth Embodiment

Next, a fourth embodiment of the present invention will be described.

In the following description, the same components and steps as those of the second embodiment are given the same reference signs as those of the second embodiment, and detailed descriptions thereof are omitted or simplified.

In the second embodiment, the display control unit 454 sets main images and sub images in different sizes but sets all of the main images in the same size and all of the sub images in the same size.

Meanwhile, in the fourth embodiment, main images are different in size from each other and sub images are different in size from each other.

The configuration of an image display system in the fourth embodiment is the same as that in the second embodiment.

Hereinafter, descriptions will be given as to only the sizes of main images and sub images in the display screen W1 in the fourth embodiment.

Figure 13:
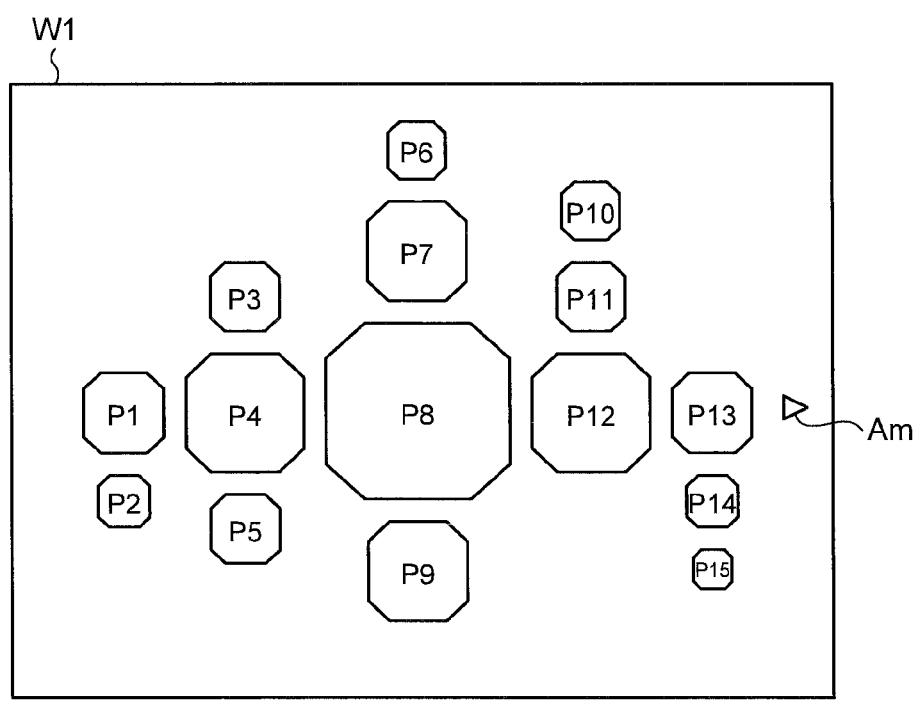
FIG. 13 is a diagram illustrating one example of a display screen generated by a display control unit according to a fourth embodiment of the present invention.

FIG. 13 is a diagram illustrating one example of the display screen W1 generated by the display control unit 454 according to the fourth embodiment of the present invention.

FIG. 13 illustrates the display screen W1 generated at step S6 described in FIG. 3.

According to the fourth embodiment, the display control unit 454 generates the display screen W1 in which main image in the center position of the display screen W1 is largest in size, and main images at positions other than the center position are smaller in size as the distance from the center position to the position of the main image is longer. With regard to main images and sub images in association with each other, the display control unit 454 also generates the display screen W1 in which the sub images are smaller in size as the length from the arrangement position of the main image to the arrangement position of the sub image is longer.

For example, as illustrated in FIG. 13, the display control unit 454 generates at step S6 the display screen W1 in which the main image P8 in the center position of the display screen W1 is largest in size, the main images P4 and P12 at the right and left of the main image P8 are smaller in size than the main image P8, and the main images P1 and P13 at the left of the main image P4 and the right of the main image P12 are smaller in size than the main images P4 and P12. With regard to the main image P8 and the sub images P6, P7, and P9 in association with each other, the display control unit 454 also generates the display screen W1 in which the sub images P7 and P9 above and below the main image P8 are smaller in size than the main image P8, and the sub image P6 above the sub image P7 is smaller in size than the sub image P7. The other size relationships between the main image P1 and the sub image P2, between the main image P4 and the sub images P3 and P5, between the main image P12 and the sub images P10 and P11, and between the main image P13 and the sub images P14 and P15 are the same as the size relationship between the main image P8 and the sub images P6, P7, and P9.

The fourth embodiment is different from the second embodiment only in the sizes of the main images and the sub images, and the two embodiments are the same in how to arrange the main images and the sub images in the display screen W1 and how to scroll the display screen W1.

The fourth embodiment described above provides advantages described below, as well as the same advantages as those of the second embodiment.

In the fourth embodiment, the display control unit 454 generates the display screen W1 in which the sub images in the second upper and lower areas Ar2U and Ar2D are smaller in size as the arrangement positions of the sub images are more distant from the first area Ar1.

Accordingly, by reducing in size the in-vivo images for display (sub images) unlikely to be unusual images, the doctor or the like can take notice of the in-vivo images for display (main images) likely to be unusual images and find unusual images in an further easier manner.

In the fourth embodiment, the display control unit 454 generates the display screen W1 in which the main image group is arranged in the first area Ar1 including the center position of the display screen W1, and the main images in the first area Ar1 are smaller in size as the arrangement positions of the main images are more distant from the center position.

Accordingly, the in-vivo image for display arranged in the display screen W1 at the position most noticed by the doctor or the like (the center position of the display screen W1) can be made largest in size, and the in-vivo images for display arranged in the display screen W1 at the positions less noticed by the doctor or the like (at outer edges of the display screen W1) can be made smallest in size. Therefore, it is possible to generate the display screen W1 in which the doctor or the like can easily observe the in-vivo images for display.

Fifth Embodiment

Next, a fifth embodiment of the present invention will be described.

In the following description, the same components and steps as those of the first embodiment are given the same reference signs as those of the first embodiment, and detailed descriptions thereof are omitted or simplified.

The fifth embodiment is different from the first embodiment only in the display screen W1 generated by operating the playback icon Am to scroll the display screen W1.

The configuration of an image display device in the fifth embodiment is the same as that in the first embodiment.

Hereinafter, descriptions will be given as to only the display screen W1 generated during scrolling according to the fifth embodiment.

Figure 14:
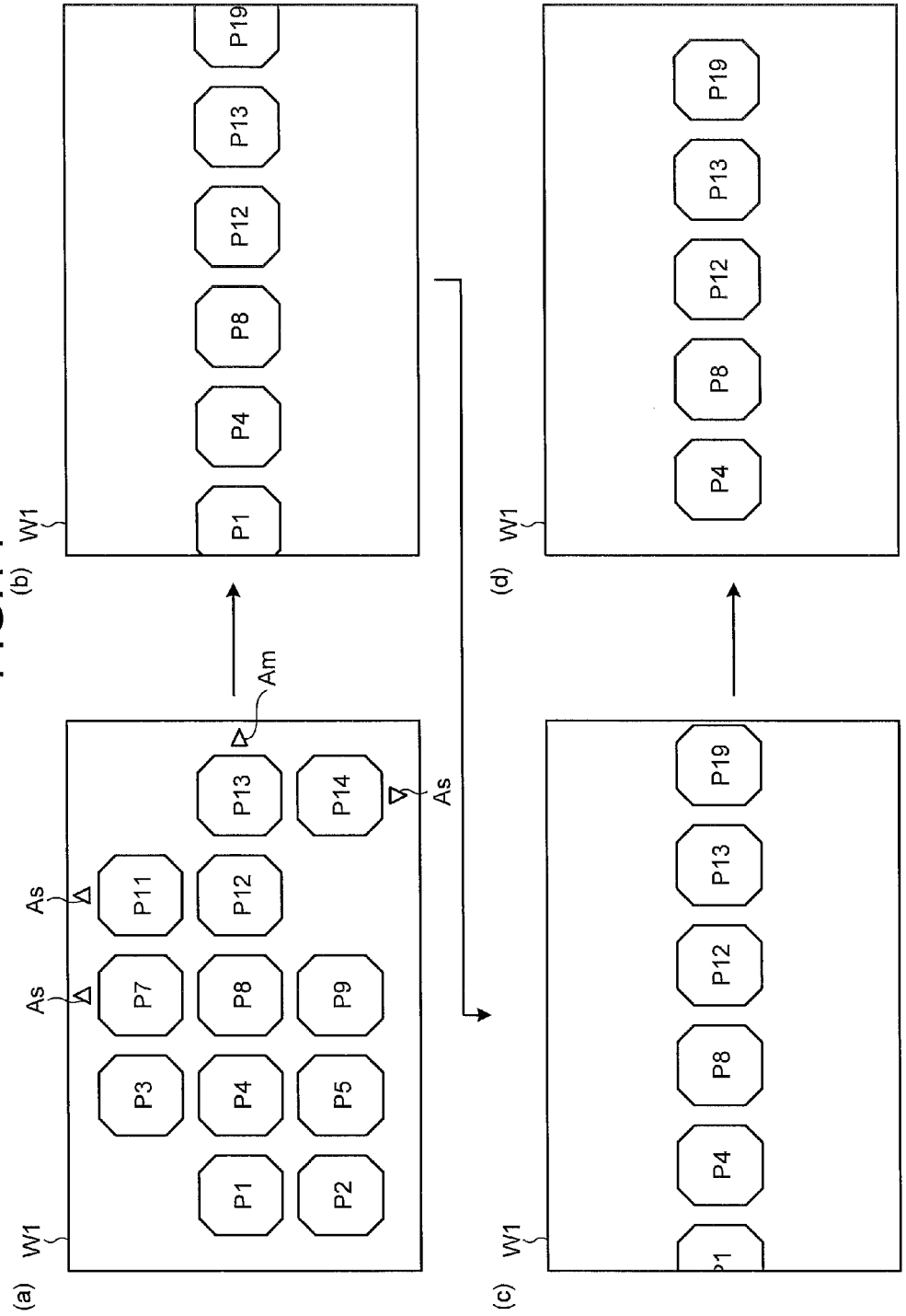
FIG. 14 is a diagram illustrating one example of screen transitions in a display screen by a display control unit according to a fifth embodiment of the present invention.

FIG. 14 is a diagram illustrating one example of screen transitions in a display screen W1 by the display control unit 454 according to the fifth embodiment of the present invention.

FIG. 14 illustrates screen transitions of the display screen W1 illustrated in FIG. 4 when the playback icon Am has been operated (the display screen W1 displayed at step S7 described in FIG. 3) ((a) of FIG. 14 is identical to FIG. 4).

In the fifth embodiment, when the playback icon Am at the left end or right end of the display screen W1 has been operated (step S8 described in FIG. 3: Yes), the display control unit 454 scrolls the display screen W1 in a mode in which the sub image group is not displayed (not arranged in the display screen W1) and the main image group is moved in the rightward or leftward direction.

For example, when the playback icon Am at the right end of the display screen W1 illustrated in FIG. 4 at step S7 has been operated, the display control unit 454 sequentially generates display screens W1 illustrated in (b) to (d) of FIG. 14 in which the sub image group is not arranged in the second upper and lower areas Ar2U and Ar2D but the main images P1, P4, P8, P12, and P13 are integrally moved to the left. Then, the display control unit 454 sequentially displays in the display unit 44 the generated display screens W1 illustrated in (b) to (d) of FIG. 14 according to the display frame rate of the display unit 44.

Figure 15:
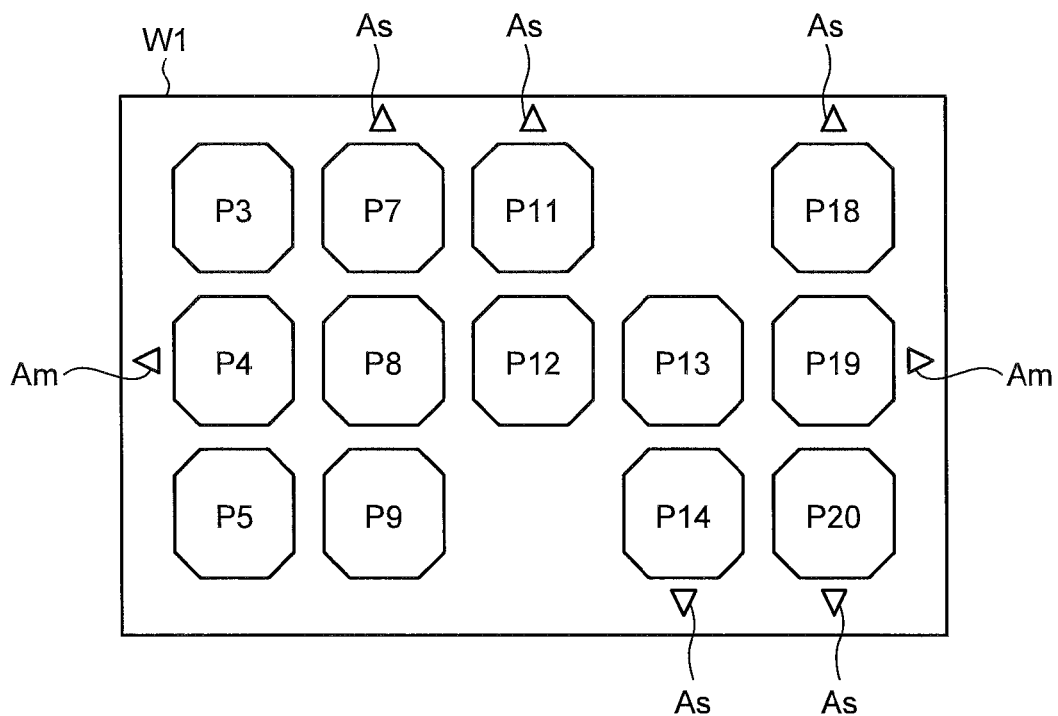
FIG. 15 is a diagram illustrating one example of a display screen generated by the display control unit according to the fifth embodiment of the present invention.

FIG. 15 is a diagram illustrating one example of the display screen W1 generated by the display control unit 454 according to the fifth embodiment of the present invention.

FIG. 15 illustrates the display screen W1 when the stop operation has been performed in the state illustrated in (d) of FIG. 14 (step S10 described in FIG. 3: Yes).

When the stop operation has been performed (step S10 described in FIG. 3: Yes) or when there is no more main image to be displayed (step S1 described in FIG. 3: No), the display control unit 454 stops scrolling of the display screen W1. Then, the display control unit 454 generates the same display screen W1 (refer to FIGS. 8 and 15) as that in the first embodiment such that the playback icons Am and As and sub images associated with main images are arranged in the display screen W1 displayed in the display unit 44 at the stop of the scrolling, and displays the display screen W1 in the display unit 44.

The fifth embodiment described above provides an advantage described below, as well as the same advantage as that of the first embodiment.

In the fifth embodiment, the display control unit 454 does not arrange the sub image group in the display screen W1 during scrolling of the display screen W1 along the first direction D1, but arranges the sub image group in the display screen W1 after the stop of scrolling.

Accordingly, during scrolling of the display screen W1 in which the main image group is arranged along the first direction D1, the sub image group not to be noticed by the doctor or the like is not displayed so that the doctor or the like can take notice of only the main image group and find unusual images in an effective manner.

Sixth Embodiment

Next, a sixth embodiment of the present invention will be described.

In the following description, the same components and steps as those of the first embodiment are given the same reference signs as those of the first embodiment, and detailed descriptions thereof are omitted or simplified.

The sixth embodiment is different from the first embodiment only in that main images are displayed in an enhanced manner in the display screen W1 so as to be distinguishable from sub images.

The configuration of an image display device in the sixth embodiment is the same as that in the first embodiment.

Hereinafter, descriptions will be given as to only enhanced display of main images in the display screen W1 according to the sixth embodiment 6.

Figure 16:
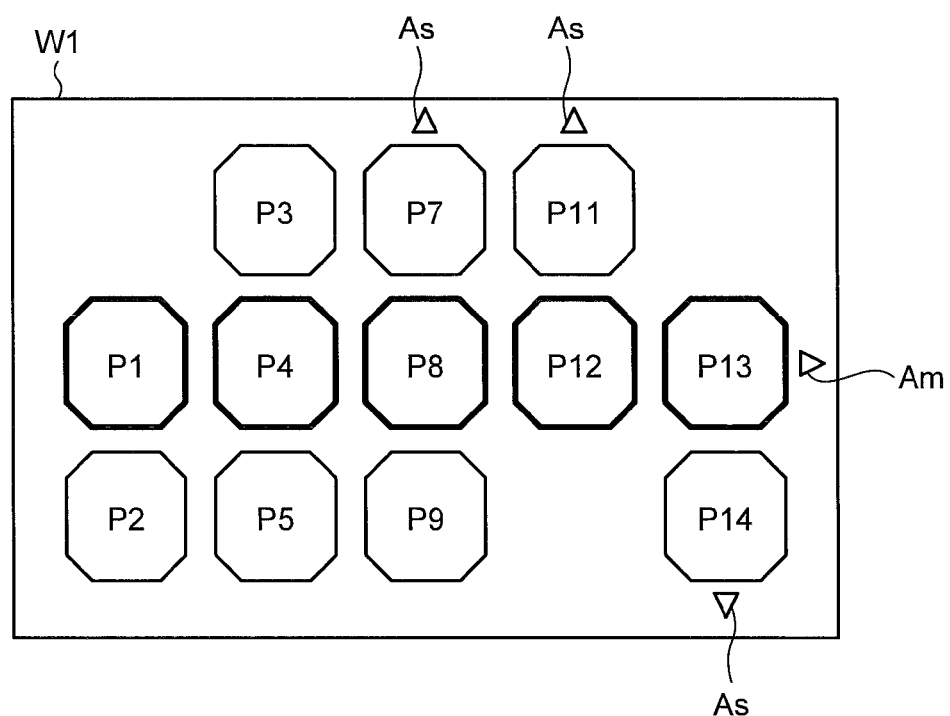
FIG. 16 is a diagram illustrating one example of a display screen generated by a display control unit according to a sixth embodiment of the present invention.

FIG. 16 is a diagram illustrating one example of the display screen W1 generated by the display control unit 454 according to the sixth embodiment of the present invention.

FIG. 16 illustrates the display screen W1 generated at step S6 described in FIG. 3.

According to the sixth embodiment, the display control unit 454 generates the display screen W1 as illustrated in FIG. 16 in which outer edges of the main images P1, P4, P8, P12, and P13 are enhanced by thick frames or the like in the display screen W1 such that the main images P1, P4, P8, P12, and P13 are distinguishable from the sub images P2, P3, P5 to P7, P9 to P11, and P14.

Although not specifically illustrated, as well as the display screen W1 generated at step S6, the display control unit 454 generates the display screen W1 in which the outer edges of the main images are enhanced by thick frames or the like when the display screen W1 is scrolled (step S9 described in FIG. 3) or when the scrolling is stopped (step S12 described in FIG. 3).

The sixth embodiment described above provides an advantage described below, as well as the same advantage as that of the first embodiment.

In the sixth embodiment, the display control unit 454 generates the display screen W1 in which main images are displayed in a more enhanced manner than sub images.

Accordingly, by displaying main images likely to be unusual images in a more enhanced manner than sub images unlikely to be unusual images, the doctor or the like can take notice of the main images and find unusual images in a further easier manner.

Seventh Embodiment

Next, a seventh embodiment of the present invention will be described.

In the following description, the same components and steps as those of the first embodiment are given the same reference signs as those of the first embodiment, and detailed descriptions thereof are omitted or simplified.

In the first embodiment described above, the display control unit 454 generates the display screen W1 in which the main images and the sub images are arranged at predetermined spacings.

Meanwhile, in the seventh embodiment, there are no spacings between the main images and sub images in the display screen W1.

The configuration of an image display system in the seventh embodiment is the same as that in the first embodiment.

Hereinafter, the display screen W1 in the seventh embodiment will be described.

Figure 17:
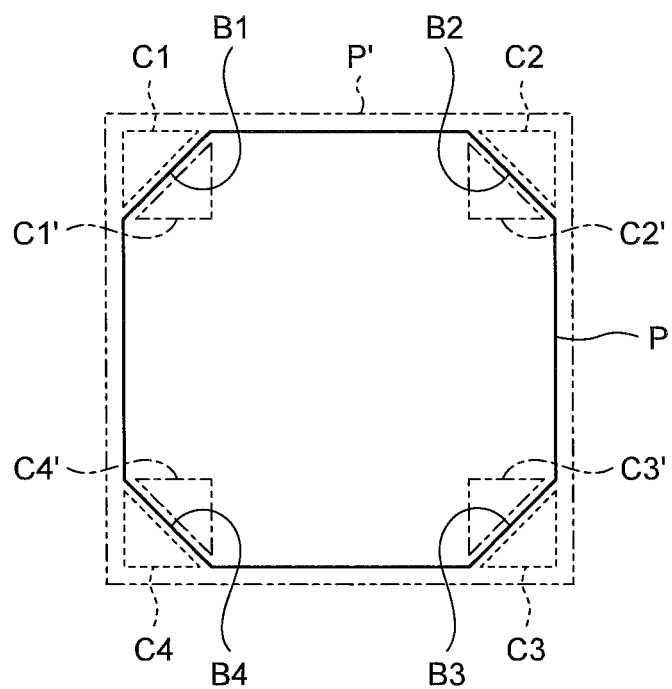
FIG. 17 is a diagram describing a method of producing a display screen in a seventh embodiment of the present invention.

FIG. 17 is a diagram describing a method of generating the display screen W1 in the seventh embodiment of the present invention.

As illustrated in FIG. 17, an in-vivo image for display P is not a rectangular image but an octagonal image without pixel data (pixel values) in areas C1 to C4 at four corners of a rectangle. Accordingly, even if an attempt is made to arrange main images and sub images without spacings in the display screen W1, clearances are formed in the area C1 to C4.

Accordingly, the image processing unit 452 in the seventh embodiment extracts pixels from areas C1' to C4' symmetrical to the four corner areas C1 to C4 with respect to boundary lines B1 to B4, for each of in-vivo images for display P included in the in-vivo image group for display, and acquires the values of the pixels.

The boundary lines B1 to B4 here refer to boundaries between the in-vivo image for display P and the four corner areas C1 to C4.

Then, the image processing unit 452 uses the acquired values of the pixels in the areas C1' to C4' to interpolate the corresponding four corner areas C1 to C4. Specifically, as a value of a given interpolated pixel in the area C1, the value of a pixel in the area C1' symmetrical to the interpolated pixel with respect to the boundary line B1 is applied. This matter on the area C1 is also applicable to the other areas C2 to C4.

As a result of the interpolation, an in-vivo image for display P' with the four corner areas C1 to C4 interpolated is generated as illustrated in FIG. 17.

Figure 18:
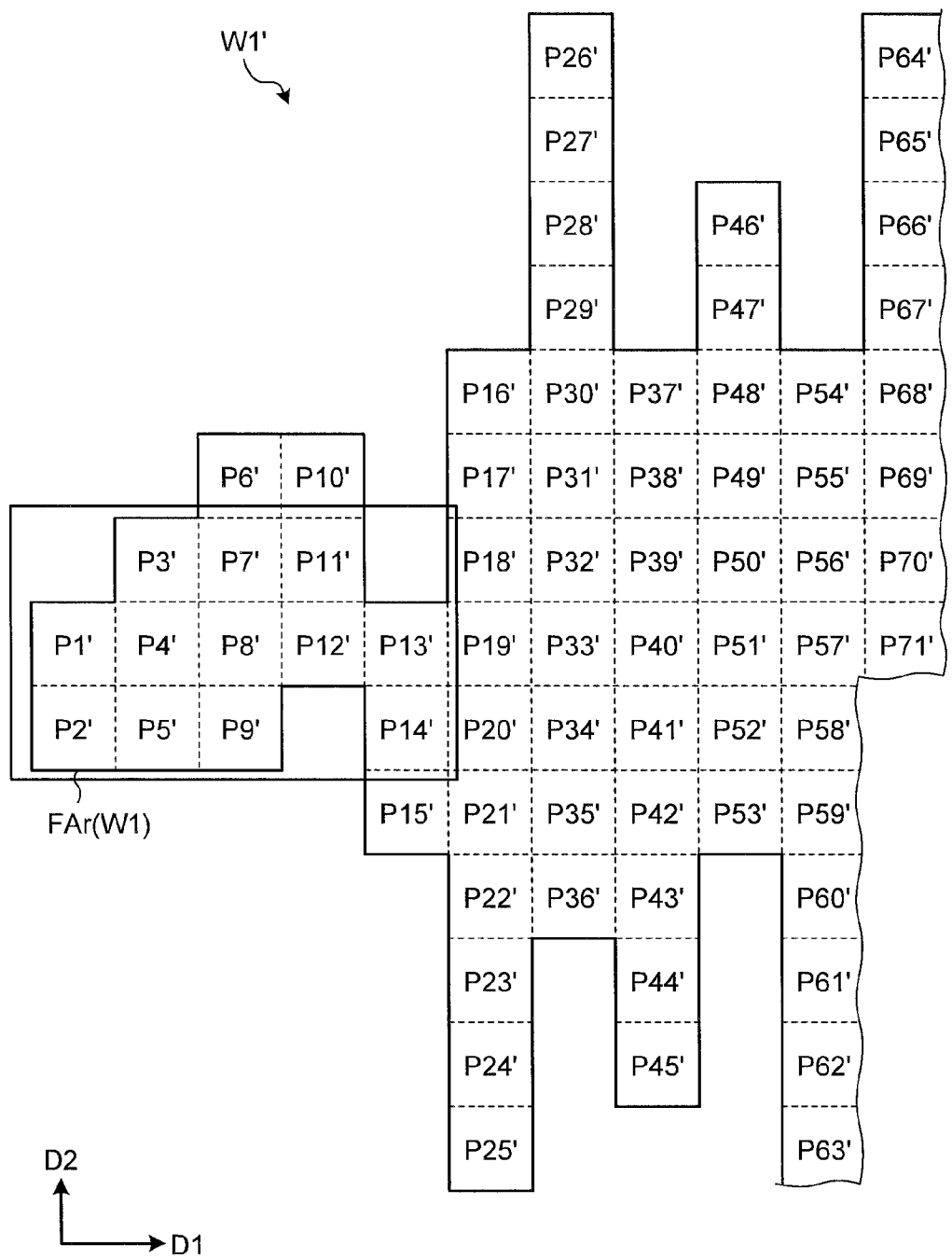
FIG. 18 is a virtual representation of a display screen generated by the display control unit according to the seventh embodiment of the present invention.

FIG. 18 is a virtual representation of the display screen W1 generated by the display control unit 454 according to the seventh embodiment of the present invention.

FIG. 18 illustrates in-vivo images for display P1' to P71' of first to 71 frames with four corner areas C1 to C4 interpolated as in the case of FIG. 7.

The display control unit 454 according to the seventh embodiment generates the display screen W1 in which the in-vivo images for display P' interpolated by the image processing unit 452 are arranged without spacings, and displays the display screen W1 in the display unit 44.

For example, when the display screen W1 generated by the display control unit 454 is virtually represented, the display screen W1 constitutes a portion of a virtual screen W1' in which the in-vivo images for display P' are arranged without spacings as illustrated in FIG. 18 (FIG. 18 illustrates only the in-vivo images for display P1' to P71').

The seventh embodiment is different from the first embodiment only in which the main images and the sub images are arranged without spacings, and the two embodiments are the same in how to arrange the main images and the sub images in the display screen W1 and how to scroll the display screen W1.

The seventh embodiment described above provides an advantage described below, as well as the same advantage as that of the first embodiment.

In the seventh embodiment, the display control unit 454 generates the display screen W1 in which there are no spacings between main images included in the main image group and between sub images included in the sub image group.

Accordingly, although, when there are spacings between the main images and the sub images in the display screen W1, the doctor or the like needs to follow each of the images with his/her eyes, the seventh embodiment has no spacings between the main images and the sub images in the display screen W1, which allows the doctor or the like to watch comprehensively the main images and the sub images arranged without spacings. Therefore, it is possible to generate the display screen W1 in which the doctor or the like can observe the in-vivo images for display in an easy manner.

Modification Example of the Seventh Embodiment

In the seventh embodiment described above, when arranging the in-vivo images for display P' without spacings in the display screen W1, the boundaries between the adjacent in-vivo images for display P' may be interpolated to make the boundaries less visible.

For example, the interpolation may be performed with the use of values of pixels in end areas of the in-vivo images for display P' adjacent to the boundaries (refer to Japanese Patent Application Laid-open No. 2012-185583, for example).

Other Embodiments

As in the foregoing, embodiments for carrying out the present invention are described. However, the present invention is not limited by the first to seventh embodiments described above.

In the first to seventh embodiments, the image display device 4 uses the recording medium 5 and the reader/writer 41 to acquire an in-vivo image group taken by the capsule endoscope 2 in a time-series manner. However, the present invention is not limited to this.

For example, an in-vivo image group is saved in advance in a separately installed server, and the image display device is provided with a communication unit to communicate with the server. Then, the image display device may cause the communication unit to communicate with the server to acquire the in-vivo image group. In this case, the image acquisition unit in the present invention is equivalent to the communication unit.

In the first to seventh embodiments described above, the image extraction condition is the threshold for degree of similarity between temporally successive in-vivo images. However, the present invention is not limited to this.

For example, the image extraction condition may be a threshold for specific color level of red or any other color in the in-vivo images, a threshold for level of an average color in the in-vivo images, or a threshold for spread level of a specific color (the number of pixels in a specific color) in the in-vivo images may be employed. In the case of such an image extraction condition, the image processing unit 452 calculates the specific color level of red or any other color in the in-vivo images, the level of an average color in the in-vivo images, or the spread level of a specific color in the in-vivo images for each of the in-vivo images for display, based on color information on the in-vivo images for display.

In the first to seventh embodiments described above, main images may be extracted from the in-vivo image group for display by any extraction method other than those in the first to seventh embodiments described above.

For example, the image display device (control unit) detects areas of interest (areas likely to include a bleeding site, a lesion, or the like) from the in-vivo images for display, based on color feature data, texture feature data, and the like of pixels in the in-vivo images for display. The image display device (control unit) also compares the areas of interest in the temporally successive in-vivo images for display, and calculates the degrees of similarity (indexes of similarity between the compared areas), the degrees of difference (indexes of difference between the compared areas), the data of movement (the data of change in coordinates at association of the same subject in the compared areas), or the data of statistics (the average, variance, skewness, kurtosis, histogram, and the like of pixel values in the compared areas). Then, the image display device (image extraction unit) extracts the in-vivo images for display with a predetermined degree of similarity, degree of difference, data of movement, or data of statistics, as main images (for the foregoing extraction method, refer to Japanese Patent Application Laid-open No. 2010-142287, for example).

In the first to seventh embodiments, the display screen W1 is scrolled when the playback icon Am or As has been operated by the user. However, the present invention is not limited to this.

For example, when the user moves the mouse while pressing and holding the mouse button, the display screen W1 may be scrolled in the direction of movement of the mouse. At that time, the speed of scrolling of the display screen W1 (the speed of movement of main images and others) may be changed according to the speed of movement of the mouse (the speed of the scrolling is higher as the mouse is moved more quickly).

Figure 19:
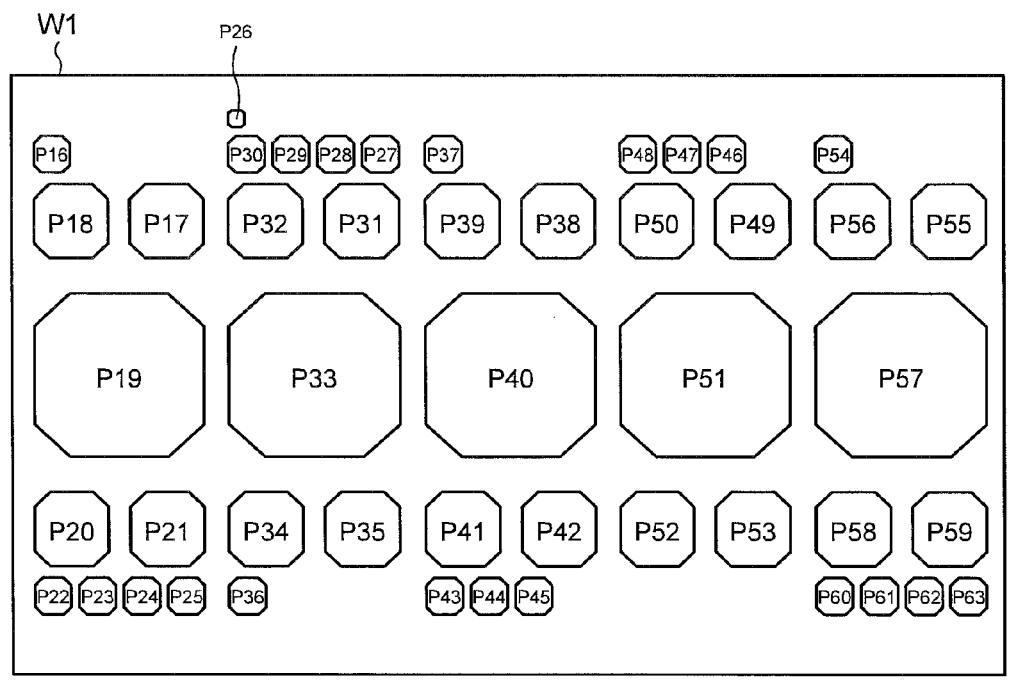
FIG. 19 is a diagram illustrating a modification example of the first to seventh embodiments of the present invention.

FIG. 19 is a diagram illustrating a modification example of the first to seventh embodiments of the present invention.

In the first to seventh embodiments, sub images associated with main images are arranged in a time-series manner along the second direction D2 orthogonal to the first direction D1 so as to be aligned with the main images. However, the present invention is not limited to this.

For example, main images and sub images may be arranged as illustrated in FIG. 19.

Hereinafter, descriptions will be given as to the arrangement relationship between a main image P33 and sub images P26 to P32 and P34 to P36 associated with the main image P33 as illustrated in FIG. 19.

Specifically, up to two each sub images with frame numbers near the frame number of the main image P33 are arranged in a size smaller than the size of the main image P33 above and below the main image P33 in the first direction (in the example of FIG. 19, the sub images P31 and P32 and the sub images P34 and P35 that will be hereinafter referred to as first sub images). In addition, up to four each sub images temporally anterior and posterior to the first sub images are arranged in a size smaller than the size of the first sub images above and below the first sub images in the first direction (in the example of FIG. 19, the sub images P27 to P30 and the sub image P36 that will be hereinafter referred to as second sub images). Further, up to eight each sub images temporally anterior and posterior to the second sub images are arranged in a size smaller than the size of the second sub images above and below the second sub images in the first direction (in the example of FIG. 19, only the sub image P26 that will be hereinafter referred to as a third sub image). When there is any image temporally anterior and posterior to the third sub image, the image is arranged in the same manner as the first to third sub images are.

The arrangement relationships between other main images and sub images associated with the main images illustrated in FIG. 19 are the same as the arrangement relationship between the main image P33 and the sub images P26 to P32 and P34 to P36 associated with the main image P33.

According to some embodiments, it is possible to display a display screen on which it is easier to find unusual images included in an image group acquired in a time-series manner even if the unusual images are limited in number.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display device comprising:
a display unit that displays a display screen;
an image extraction unit that extracts a main image group from an image group, the image group including a plurality of images acquired in a time-series manner, and the main image including main images satisfying a specified condition;
an image association unit that associates each of sub images included in a sub image group not extracted by the image extraction unit from the image group with each of the main images included in the main image group; and
a display control unit that generates a display screen in which the main image group is arranged in a first area in a time-series manner along a first direction and each of the sub images associated with each of the main images by the image association unit is aligned with each of the main images in a second area different from the first area in a time-series manner along a second direction orthogonal to the first direction, and causes the display unit to display the display screen, wherein the display control unit changes the display screen in a mode in which the main image group is moved along the first direction and in a mode in which at least part of the main image group and at least part of the sub image group are moved along the second direction.

2. The image display device according to claim 1, wherein the image association unit associates each of the sub images with each of the main images temporally nearest each of the sub images.

3. The image display device according to claim 1, wherein the display control unit generates the display screen in which the sub images are smaller in size than the main images.

4. The image display device according to claim 1, wherein the display control unit generates the display screen in which the sub images are smaller in size as arrangement positions of the sub images in the second area are more distant from the first area.

5. The image display device according to claim 1, wherein the display control unit generates the display screen in which the main image group is arranged in the first area including a center position of the display screen, and the main images are smaller in size as arrangement positions of the main images in the first area are more distant from the center position.

6. The image display device according to claim 1, further comprising an instruction acceptance unit that accepts an instruction for starting change of the display screen in the mode in which the main image group is moved along the first direction, and accepts an instruction for stopping the change of the display screen in the mode in which the main image group is moved along the first direction, wherein
when the instruction acceptance unit accepts the instruction for starting, the display control unit sequentially generates the display screen in a mode in which the main image group is moved along the first direction without arrangement of the sub image group in the second area, and
when the instruction acceptance unit accepts the instruction for stopping, the display control unit generates the display screen in a mode in which the sub image group is arranged in the second area and the movement of the main image group is stopped.

7. The image display device according to claim 1, wherein the display control unit generates the display screen in which there are no spacings between the main images included in the main image group and the sub images included in the sub image group.

8. The image display device according to claim 1, wherein the display control unit generates the display screen in which the main images are displayed in an enhanced manner as compared to the sub images.

9. The image display device according to claim 1, wherein, when all of the main images included in the main image group are not arranged in the display screen, the display control unit includes in the display screen existence information indicating existence of the main images not arranged.

10. The image display device according to claim 9, wherein the existence information refers to information indicating the number of the main images not arranged.

11. The image display device according to claim 1, wherein, when all of the sub images included in the sub image group are not arranged in the display screen, the display control unit includes in the display screen existence information indicating existence of the sub images not arranged.

12. The image display device according to claim 11, wherein the existence information refers to information indicating the number of the sub images not arranged.

13. An image display method executed by an image display device, comprising:
extracting a main image group from an image group, the image group including a plurality of images acquired in a time-series manner, and the main image including main images satisfying a specified condition;
associating each of sub images included in a sub image group not extracted from the image group with each of the main images included in the main image group;
generating a display screen in which the main image group is arranged in a first area in a time-series manner along a first direction and each of the sub images associated with each of the main images is aligned with each of the main images in a second area different from the first area in a time-series manner along a second direction orthogonal to the first direction;
displaying the display screen; and
changing the display screen, wherein,
in the changing the display screen, the display screen is changed in a mode in which the main image group is moved along the first direction and in a mode in which at least part of the main image group and at least part of the sub image group are moved along the second direction.

14. A non-transitory computer-readable recording medium having an executable program recorded therein, the program instructing a processor, which an image display device has, to execute:
extracting a main image group from an image group, the image group including a plurality of images acquired in a time-series manner, and the main image including main images satisfying a specified condition;
associating each of sub images included in a sub image group not extracted from the image group with each of the main images included in the main image group;
generating a display screen in which the main image group is arranged in a first area in a time-series manner along a first direction and each of the sub images associated with each of the main images is aligned with each of the main images in a second area different from the first area in a time-series manner along a second direction orthogonal to the first direction;
displaying the display screen; and
changing the display screen, wherein,
in the changing the display screen, the display screen is changed in a mode in which the main image group is moved along the first direction and in a mode in which at least part of the main image group and at least part of the sub image group are moved along the second direction.

* * * * *